(12) United States Patent
Morgan

(10) Patent No.: US 9,181,192 B2
(45) Date of Patent: *Nov. 10, 2015

(54) DEUTERATED CFTR POTENTIATORS

(71) Applicant: Concert Pharmaceuticals, Inc., Lexington, MA (US)

(72) Inventor: Adam J. Morgan, Ashland, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/490,787

(22) Filed: Sep. 19, 2014

(65) Prior Publication Data

US 2015/0099780 A1 Apr. 9, 2015

Related U.S. Application Data

(63) Continuation of application No. 14/082,843, filed on Nov. 18, 2013, now Pat. No. 8,865,902, and a continuation-in-part of application No. PCT/US2012/038297, filed on May 17, 2012.

(60) Provisional application No. 61/860,602, filed on Jul. 31, 2013, provisional application No. 61/780,681, filed on Mar. 13, 2013, provisional application No. 61/727,941, filed on Nov. 19, 2012, provisional application No. 61/487,497, filed on May 18, 2011.

(51) Int. Cl.
*A61K 31/47* (2006.01)
*C07D 215/00* (2006.01)
*C07D 215/56* (2006.01)

(52) U.S. Cl.
CPC .................................. *C07D 215/56* (2013.01)

(58) Field of Classification Search
None
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 8,865,902 B2 * | 10/2014 | Morgan | 546/156 |
| 2006/0074075 A1 | 4/2006 | Hadida-Ruah et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| WO | 95/26325 A2 | 10/1995 |
| WO | 2007079139 A2 | 7/2007 |
| WO | 2007/118651 A1 | 10/2007 |
| WO | 2012158885 A1 | 11/2012 |

OTHER PUBLICATIONS

Baille, T. A., "The Use of Stable Isotopes in Pharmacological Research," Pharmacological Reviews, 33(2): 81-132 (1981).
Browne, T. R., "Stable Isotope Techniques in Early Drug Development: An Economic Evaluation," J. Clin. Pharmacol., 38: 213-220 (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
Dyck, L. E., et al., "Effects of Deuterium Substitution on the Catabolism of ?-Phenylethylamine: An In Vivo Study," Journal of Neurochemistry, 46(2): 399-404 (1986).
Foster, A. B., "Deuterium Isotope Effects in Studies of Drug Metabolism," Trends in Pharmacological Sciences, 5: 524-527 (1984).
Foster, A. B., "Deuterium Isotope Effects in the Metabolism of Drugs and Xenobiotics: Implications for Drug Design," Advances in Drug Research, 14: 1-40 (1985).
Gouyette, A., "Synthesis of Deuterium-labelled Elliptinium and its Use in Metabolic Studies," Biomedical and Environmental Mass Spectrometry, 15: 243-247 (1988).
Haskins, N. J., "The Application of Stable Isotopes in Biomedical Research," Biomedical Mass Spectrometry, 9(7): 269-277 (1982).
Honma S., et al., "The metabolism of roxatidine acetate hydrochloride. Liberation of deuterium from the piperidine ring during hydroxylation," Drug Metabolism and Disposition, 15(4): 551-559 (1987).
Pieniaszek, H. J., et al., "Moricizine Bioavailability via Simultaneous, Dual, Stable Isotope Administration: Bioequivalence Implications," J. Clin. Pharmacol, 39: 817-825 (1999).

(Continued)

*Primary Examiner* — Heidi Reese
(74) *Attorney, Agent, or Firm* — McCarter & English, LLP; Steven G. Davis; Emily Dertz

(57) ABSTRACT

This invention relates to compounds of Formula I:

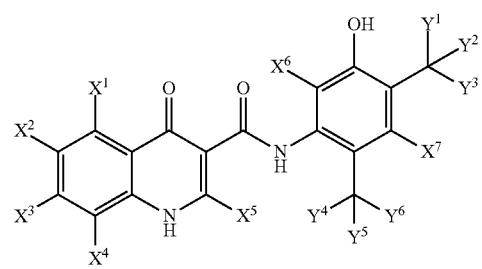

Formula I and pharmaceutically acceptable salts thereof. This invention also provides compositions comprising a compound of this invention and the use of such compositions in methods of treating diseases and conditions that are beneficially treated by administering a CFTR potentiator.

18 Claims, 1 Drawing Sheet

(56) References Cited

OTHER PUBLICATIONS

Tonn G. R., et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometry, 22: 633-642 (1993).

Wolen, R. L., "The Application of Stable Isotopes to Studies of Drug Bioavailability and Bioequivalence," J. Clin. Pharmacol., 26: 419-424 (1986).

Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).

Kushner, D.J. et al., "Pharmacological Uses and Perspectives of Heavy Water and Deuterated Compounds," Can. J. Physiol. Pharmacol., 77:79-88 (1999).

Buteau, K.C., Deuteraed Drugs: Unexpectedly Nonobvious?, Journal of High Technology Law, Suffical University Law School, X(1):22-74; Jan. 2009.

U.S. FDA, Center for Drug Evaluation and Research: IVACAFTOR (VX-770), Application No. NDA 203-188Orig1s000, Clinical Pharmacology and Biopharmaceutics Reviews(s), pp. 1-102 Jan. 18, 2012.

O'Driscoll, Cath, Heavyweight Drugs, Swapping Selected Hydrogen Atoms for Deuterium Could Be a Fast Route to Making Safer, Longer Lasting Drugs; Chemistry & Industry, pp. 24-26; Mar. 9, 2009.

Concert Pharmaceuticals, Inc., Precision Deuterium Chemistry Backgrounder, pp. 1-6; 2007.

Chen, Yingxue, et al., Drug-Drug Interaction Between VX770 and CYP3A Modulators, J. Clinical Pharmacol; 51:1348, 2011.

U.S. FDA: Kalydeco™ (Ivacaftor) Tablets; Jan. 2012.

* cited by examiner

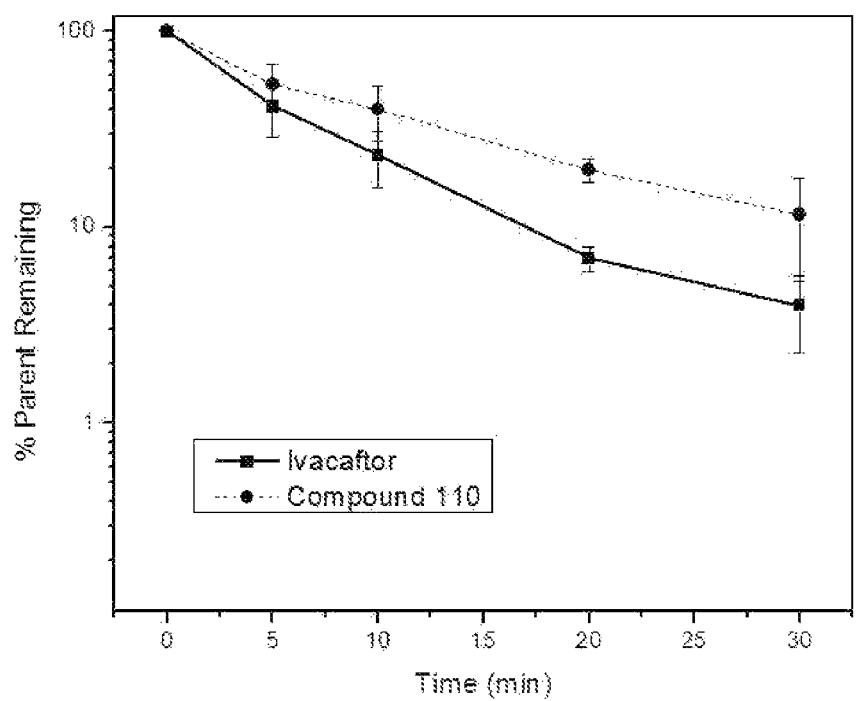

DEUTERATED CFTR POTENTIATORS

RELATED APPLICATIONS

This application is a continuation of U.S. application Ser. No. 14/082,843, filed Nov. 18, 2013, which is a continuation-in-part of International Application No. PCT/US12/38297, filed May 17, 2012, which claims the benefit of U.S. Provisional Application Ser. No. 61/487,497, filed May 18, 2011. This application also claims the benefit of U.S. Provisional Application Ser. No. 61/727,941, filed Nov. 19, 2012; U.S. Provisional Application Ser. No. 61/780,681, filed Mar. 13, 2013; and U.S. Provisional Application Ser. No. 61/860,602, filed Jul. 31, 2013. The contents of these applications are incorporated herein by reference in their entirety.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res, 1985, 14:1-40 ("Foster"); Kushner, D J et al, Can J Physiol Pharmacol, 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem., 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel derivatives of ivacaftor, and pharmaceutically acceptable salts thereof. This invention also provides compositions comprising a compound of this invention and the use of such compositions in methods of treating diseases and conditions that are beneficially treated by administering a CFTR (cystic fibrosis transmembrane conductance regulator) potentiator.

Ivacaftor, also known as VX-770 and by the chemical name, N-(2,4-di-tert-butyl-5-hydroxyphenyl)-4-oxo-1,4-dihydroquinoline-3-carboxamide, acts as a CFTR potentiator. Results from phase III trials of VX-770 in patients with cystic fibrosis carrying at least one copy of the G551D-CFTR mutation demonstrated marked levels of improvement in lung function and other key indicators of the disease including sweat chloride levels, likelihood of pulmonary exacerbations and body weight. VX-770 is also currently in phase II clinical trials in combination with VX-809 (a CFTR corrector) for the oral treatment of cystic fibrosis patients who carry the more common ΔF508-CFTR mutation. VX-770 was granted fast track designation and orphan drug designation by the FDA in 2006 and 2007, respectively.

Despite the beneficial activities of VX-770, there is a continuing need for new compounds to treat the aforementioned diseases and conditions.

BRIEF DESCRIPTION OF THE DRAWINGS

FIG. 1 depicts the percentage of compound remaining over time for Compound 110 of the invention and for ivacaftor in human cytochrome P450-specific SUPERSOMES™.

DEFINITIONS

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of VX-770 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure.

The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

THERAPEUTIC COMPOUNDS

The present invention provides a compound of Formula I:

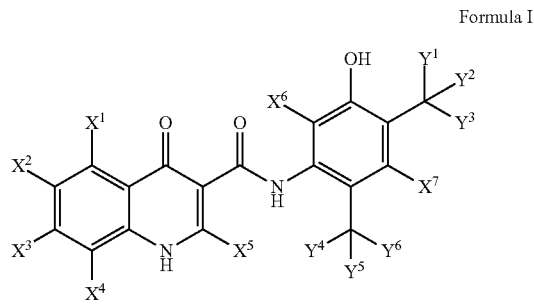

Formula I or a pharmaceutically acceptable salt thereof, wherein
each of $X^1$, $X^2$, $X^3$, $X^4$, $X^5$, $X^6$, and $X^7$ is independently hydrogen or deuterium;
each of $Y^1$, $Y^2$, $Y^3$, $Y^4$, $Y^5$, and $Y^6$ is independently $CH_3$ or $CD_3$;
provided that if each of $Y^1$, $Y^2$, $Y^3$, $Y^4$, $Y^5$, and $Y^6$ is $CH_3$, then at least one of $X^1$, $X^2$, $X^3$, $X^4$, $X^5$, $X^6$, and $X^7$ is deuterium.

In one embodiment, $X^1$, $X^2$, $X^3$, and $X^4$ are the same. In one aspect of this embodiment, $X^6$ and $X^7$ are the same. In one aspect of this embodiment, $Y^1$, $Y^2$, and $Y^3$ are the same. In one aspect of this embodiment, $Y^4$, $Y^5$, and $Y^6$ are the same. In one example of this aspect, $Y^1$, $Y^2$, and $Y^3$ are the same. In a more particular example, $X^6$ and $X^7$ are the same.

In one embodiment, each of $Y^1$, $Y^2$, and $Y^3$ is the same. In one aspect of this embodiment, each of $Y^4$, $Y^5$, and $Y^6$ is the same. In one example of this aspect, $X^6$ and $X^7$ are the same.

embodiment, $Y^1$, $Y^2$, and $Y^3$ are $CH_3$. In yet another embodiment, $Y^1$, $Y^2$, $Y^3$, $Y^4$, $Y^5$, and $Y^6$ are $CD_3$. In yet another embodiment, $Y^1$, $Y^2$, $Y^3$, $Y^4$, $Y^5$, and $Y^6$ are $CH_3$. In one aspect of any embodiment wherein $Y^1$, $Y^2$, and $Y^3$ are $CD_3$, $X^6$ is hydrogen. In one example of this aspect, $X^7$ is hydrogen. In another example of this aspect, $X^7$ is deuterium. In one aspect of any embodiment wherein $Y^1$, $Y^2$, and $Y^3$ are $CD_3$, $X^6$ is deuterium. In one example of this aspect, $X^7$ is hydrogen. In another example of this aspect, $X^7$ is deuterium. In one aspect of the embodiment wherein $Y^1$, $Y^2$, and $Y^3$ are $CD_3$ and $X^6$ is deuterium, the isotopic enrichment factor for $X^6$ is at least 4000 (60% deuterium incorporation), such as at least 4500 (67.5% deuterium incorporation), such as at least 5000 (75% deuterium), but not greater than 5500 (82.5% deuterium incorporation).

In one aspect of any embodiment wherein $Y^1$, $Y^2$, and $Y^3$ are $CH_3$, $Y^4$, $Y^5$, and $Y^6$ are $CD_3$ and $X^6$ is hydrogen. In one example of this aspect, $X^7$ is hydrogen. In another example of this aspect, $X^7$ is deuterium. In one aspect of any embodiment wherein $Y^1$, $Y^2$, and $Y^3$ are $CH_3$, $Y^4$, $Y^5$, and $Y^6$ are $CD_3$ and $X^6$ is deuterium. In one example of this aspect, $X^7$ is hydrogen. In another example of this aspect, $X^7$ is deuterium. In one aspect of any embodiment wherein $Y^1$, $Y^2$, and $Y^3$ are $CD_3$, $Y^4$, $Y^5$, and $Y^6$ are $CD_3$ and $X^6$ is deuterium. In one example of this aspect, $X^7$ is hydrogen. In another example of this aspect, $X^7$ is deuterium. In one aspect of the embodiment wherein $Y^1$, $Y^2$, and $Y^3$ are $CH_3$, $Y^4$, $Y^5$, and $Y^6$ are $CD_3$, and $X^6$ is deuterium, the isotopic enrichment factor for $X^6$ is at least 4000 (60% deuterium incorporation), such as at least 4500 (67.5% deuterium incorporation), such as at least 5000 (75% deuterium), but not greater than 5500 (82.5% deuterium incorporation).

In one aspect of the embodiment wherein $Y^1$, $Y^2$, $Y^3$, $Y^4$, $Y^5$, and $Y^6$ are $CH_3$, $X^6$ is deuterium. In one aspect of the embodiment wherein $Y^1$, $Y^2$, $Y^3$, $Y^4$, $Y^5$, and $Y^6$ are $CH_3$, and $X^6$ is deuterium, the isotopic enrichment factor for $X^6$ is at least 4000 (60% deuterium incorporation), such as at least 4500 (67.5% deuterium incorporation), such as at least 5000 (75% deuterium), but not greater than 5500 (82.5% deuterium incorporation).

In one embodiment, each of $Y^4$, $Y^5$, and $Y^6$ is the same. In one aspect of this embodiment, $X^6$ and $X^7$ are the same.

In one example of any of the foregoing embodiments, aspects or examples, $X^5$ is hydrogen. In another example, $X^5$ is deuterium.

In one embodiment, the compound of Formula I is any one of the compounds of table 1,

TABLE 1

| Cmpd # | $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|---|
| 100 | D | D | D | D | D | D | D | $CD_3$ | $CD_3$ | $CD_3$ | $CD_3$ | $CD_3$ | $CD_3$ |
| 101 | H | H | H | H | D | H | H | $CD_3$ | $CD_3$ | $CD_3$ | $CD_3$ | $CD_3$ | $CD_3$ |
| 102 | H | H | H | H | D | H | H | $CD_3$ | $CD_3$ | $CD_3$ | $CH_3$ | $CH_3$ | $CH_3$ |
| 103 | H | H | H | H | D | H | H | $CH_3$ | $CH_3$ | $CH_3$ | $CD_3$ | $CD_3$ | $CD_3$ |
| 104 | H | H | H | H | D | H | H | $CH_3$ | $CH_3$ | $CH_3$ | $CH_3$ | $CH_3$ | $CH_3$ |
| 105 | H | H | H | H | H | H | H | $CD_3$ | $CD_3$ | $CD_3$ | $CD_3$ | $CD_3$ | $CD_3$ |
| 106 | H | H | H | H | H | H | H | $CD_3$ | $CD_3$ | $CD_3$ | $CH_3$ | $CH_3$ | $CH_3$ |
| 107 | H | H | H | H | H | H | H | $CH_3$ | $CH_3$ | $CH_3$ | $CD_3$ | $CD_3$ | $CD_3$ |

In one embodiment, at least one of $C(Y^1)(Y^2)(Y^3)$ and $C(Y^4)(Y^5)(Y^6)$ is $C(CD_3)_3$.

In one embodiment, $Y^1$, $Y^2$, and $Y^3$ are $CD_3$. In one aspect of this embodiment, $Y^4$, $Y^5$, and $Y^6$ are $CH_3$. In another embodiment, $Y^4$, $Y^5$, and $Y^6$ are $CD_3$. In one aspect of this or a pharmaceutically acceptable salt thereof, wherein any atom not designated as deuterium is present at its natural isotopic abundance.

In one embodiment, the compound of Formula I is any one of the compounds of table 2,

TABLE 2

| Cmpd # | X¹ | X² | X³ | X⁴ | X⁵ | X⁶ | X⁷ | Y¹ | Y² | Y³ | Y⁴ | Y⁵ | Y⁶ |
|---|---|---|---|---|---|---|---|---|---|---|---|---|---|
| 110 | H | H | H | H | H | D | D | CD₃ | CD₃ | CD₃ | CD₃ | CD₃ | CD₃ |
| 111 | H | H | H | H | D | D | D | CD₃ | CD₃ | CD₃ | CD₃ | CD₃ | CD₃ |
| 112 | H | H | H | H | D | D | D | CD₃ | CD₃ | CD₃ | CH₃ | CH₃ | CH₃ |
| 113 | H | H | H | H | D | D | D | CH₃ | CH₃ | CH₃ | CD₃ | CD₃ | CD₃ |
| 114 | H | H | H | H | D | D | D | CH₃ | CH₃ | CH₃ | CH₃ | CH₃ | CH₃ |
| 115 | H | H | H | H | H | D | D | CD₃ | CD₃ | CD₃ | CD₃ | CD₃ | CD₃ |
| 116 | H | H | H | H | H | H | D | CH₃ | CH₃ | CH₃ | CD₃ | CD₃ | CD₃ |
| 117 | D | D | D | D | D | D | D | CD₃ | CD₃ | CD₃ | CH₃ | CH₃ | CH₃ |
| 118 | D | D | D | D | D | D | D | CH₃ | CH₃ | CH₃ | CD₃ | CD₃ | CD₃ |
| 119 | D | D | D | D | D | H | H | CD₃ | CD₃ | CD₃ | CH₃ | CH₃ | CH₃ |
| 120 | D | D | D | D | D | H | H | CH₃ | CH₃ | CH₃ | CD₃ | CD₃ | CD₃ |
| 121 | H | H | H | H | H | H | D | CD₃ | CD₃ | CD₃ | CD₃ | CD₃ | CD₃ |
| 122 | H | H | H | H | H | H | D | CD₃ | CD₃ | CD₃ | CH₃ | CH₃ | CH₃ |
| 123 | H | H | H | H | H | H | D | CH₃ | CH₃ | CH₃ | CD₃ | CD₃ | CD₃ |
| 124 | H | H | H | H | H | D | H | CD₃ | CD₃ | CD₃ | CD₃ | CD₃ | CD₃ |
| 125 | H | H | H | H | H | D | H | CD₃ | CD₃ | CD₃ | CH₃ | CH₃ | CH₃ |
| 126 | H | H | H | H | H | D | H | CH₃ | CH₃ | CH₃ | CD₃ | CD₃ | CD₃ | or a pharmaceutically acceptable salt thereof, wherein any atom not designated as deuterium is present at its natural isotopic abundance.

In one embodiment, the compound of Formula I is any one of the compounds of table 3,

TABLE 3

| Cmpd # | X¹ | X² | X³ | X⁴ | X⁵ | X⁶ | X⁷ | Y¹ | Y² | Y³ | Y⁴ | Y⁵ | Y⁶ |
|---|---|---|---|---|---|---|---|---|---|---|---|---|---|
| 301 | D | D | D | D | D | H | H | CD₃ | CD₃ | CD₃ | CD₃ | CD₃ | CD₃ |
| 302 | D | D | D | D | D | D | D | CH₃ | CH₃ | CH₃ | CH₃ | CH₃ | CH₃ |
| 303 | D | D | D | D | D | H | H | CH₃ | CH₃ | CH₃ | CH₃ | CH₃ | CH₃ |
| 304 | D | D | D | D | H | D | D | CD₃ | CD₃ | CD₃ | CD₃ | CD₃ | CD₃ |
| 305 | D | D | D | D | H | H | H | CD₃ | CD₃ | CD₃ | CD₃ | CD₃ | CD₃ |
| 306 | D | D | D | D | H | D | D | CH₃ | CH₃ | CH₃ | CH₃ | CH₃ | CH₃ |
| 307 | D | D | D | D | H | H | H | CH₃ | CH₃ | CH₃ | CH₃ | CH₃ | CH₃ |
| 308 | H | H | H | H | H | D | D | CH₃ | CH₃ | CH₃ | CH₃ | CH₃ | CH₃ | or a pharmaceutically acceptable salt thereof, wherein any atom not designated as deuterium is present at its natural isotopic abundance.

In one embodiment, $X^7$ is deuterium wherein the isotopic enrichment factor for $X^7$ is between 66.7 (1% deuterium incorporation) and 1333.3 (20% deuterium incorporation), such as between 333.3 (5% deuterium incorporation) and 1000 (15% deuterium incorporation), such as between 500 (7.5% deuterium incorporation) and 833.3 (12.5% deuterium incorporation), such as 666.7 (10% deuterium incorporation) or as 733.3 (11% deuterium incorporation). In one aspect of this embodiment, $Y^1$, $Y^2$, and $Y^3$ are each $CH_3$, $Y^4$, $Y^5$, and $Y^6$ are each $CD_3$ and $X^6$ is hydrogen. In one aspect of this embodiment, $Y^1$, $Y^2$, and $Y^3$ are each $CH_3$, $Y^4$, $Y^5$, and $Y^6$ are each $CD_3$ and $X^6$ is deuterium. In one aspect of this embodiment, $Y^1$, $Y^2$, and $Y^3$ are each $CD_3$, $Y^4$, $Y^5$, and $Y^6$ are each $CD_3$ and $X^6$ is hydrogen. In one aspect of this embodiment, $Y^1$, $Y^2$, and $Y^3$ are each $CD_3$, $Y^4$, $Y^5$, and $Y^6$ are each $CD_3$ and $X^6$ is deuterium. In one aspect of this embodiment, $Y^1$, $Y^2$, and $Y^3$ are each $CD_3$, $Y^4$, $Y^5$, and $Y^6$ are each $CH_3$ and $X^6$ is hydrogen. In one aspect of this embodiment, $Y^1$, $Y^2$, and $Y^3$ are each $CD_3$, $Y^4$, $Y^5$, and $Y^6$ are each $CH_3$ and $X^6$ is deuterium.

In another set of embodiments, any atom not designated as deuterium in any of the embodiments, examples or aspects set forth above is present at its natural isotopic abundance.

In another embodiment, the invention is directed to a compound selected from the group consisting of:

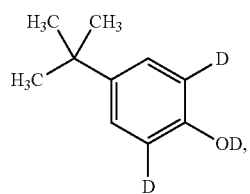

11b

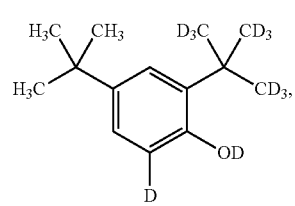

11c

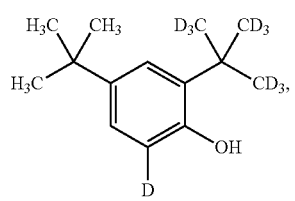

11c'

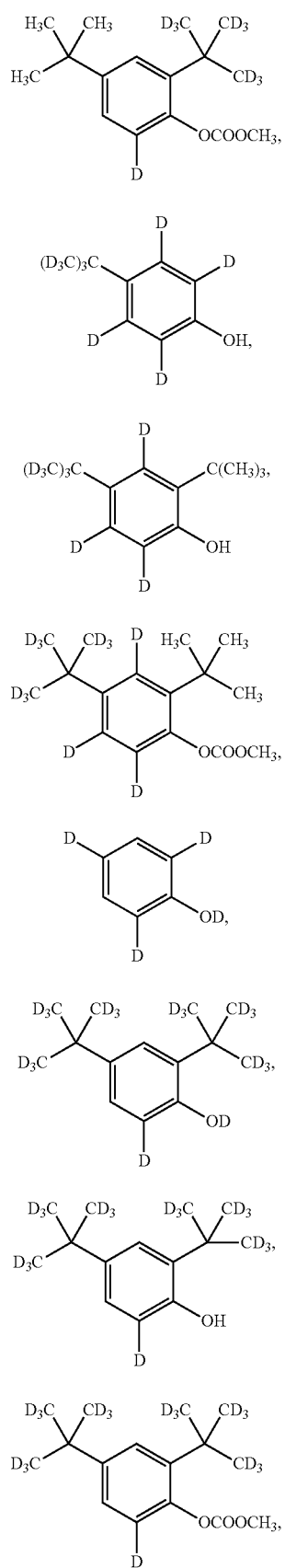

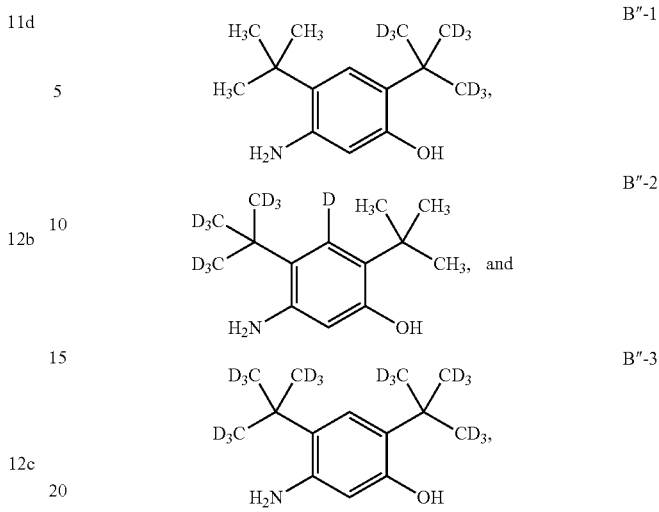

or a salt thereof,
wherein any atom not designated as deuterium is present at its natural isotopic abundance.

In one aspect of compound 11c, 11c', 12c, 13c, or 13c', the percentage of isotopic enrichment at the CD ortho to the phenolic oxygen is about 70%, In one aspect of compound 11d, 12d, or 13d, the percentage of isotopic enrichment at the CD ortho to the $OCOOCH_3$ is about 70%, In another embodiment, the invention is directed to a process comprising one or more of the following:
  i) treating 11a with a source of deuterium, such as DX, wherein X is OH, OD or halo such as Cl, to form 11b;
  ii) treating 11b with a source of $—C(CD_3)_3$, such as $X—C(CD_3)_3$, wherein X is OH, OD or halo such as Cl, to form 11c;
  iii) treating 11b with an acyloxcarbonylating agent, such as $X—C(O)OCH_3$, wherein X is OH or halo such as Cl, to form 11d;
  iv)
    (I) treating 11d with a nitrating agent, such as $HNO_3/H_2SO_4$ to form a nitroaryl compound;
    (II) treating the compound formed in (I) with a deprotecting agent, such as sodium or potassium hydroxide in an alcohol such as methanol to form a deprotected compound;
    (III) treating the compound formed in (II) with a reducing agent, such as ammonium formate and palladium over carbon to form an aminoaryl compound;
    (IV) treating the compound formed in (III) with a reducing agent, with an acid such as HX, wherein X is halo such as Cl, to form B"-1.

In another embodiment, the invention is directed to a process comprising one or more of the following:
  i. treating 12a with a source of $—C(CD_3)_3$, such as $X—C(CD_3)_3$, wherein X is OH, OD or halo such as Cl, to form 12b;
  ii. treating 12b with a source of $—C(CH_3)_3$, such as $X—C(CH_3)_3$, wherein X is OH or halo such as Cl, to form 12c;
  iii. treating 12c with an acyloxcarbonylating agent, such as $X—C(O)OCH_3$, wherein X is OH or halo such as Cl, to form 12d;
  iv.
    I. treating 12d with a nitrating agent, such as $HNO_3/H_2SO_4$ to form a nitroaryl compound;

II. treating the compound formed in (I) with a deprotecting agent, such as sodium or potassium hydroxide in an alcohol such as methanol to form a deprotected compound;

III. treating the compound formed in (II) with a reducing agent, such as ammonium formate and palladium over carbon to form an aminoaryl compound;

IV. treating the compound formed in (III) with a reducing agent, with an acid such as HX, wherein X is halo such as Cl, to form B"-2.

In another embodiment, the invention is directed to a process comprising one or more of the following:

i. treating 13a with a source of deuterium, such as DX, wherein X is OH, OD or halo such as Cl, to form 13b;
ii. treating 13c with a source of —C(CD$_3$)$_3$, such as X—C(CD$_3$)$_3$, wherein X is OH, OD or halo such as Cl, to form 13c;
iii. treating 13c with an acyloxcarbonylating agent, such as X—C(O)OCH$_3$, wherein X is OH or halo such as Cl, to form 13d;
iv.
  I. treating 13d with a nitrating agent, such as HNO$_3$/H$_2$SO$_4$ to form a nitroaryl compound;
  II. treating the compound formed in (I) with a deprotecting agent, such as sodium or potassium hydroxide in an alcohol such as methanol to form a deprotected compound;
  III. treating the compound formed in (II) with a reducing agent, such as ammonium formate and palladium over carbon to form an aminoaryl compound;
  IV. treating the compound formed in (III) with a reducing agent, with an acid such as HX, wherein X is halo such as Cl, to form B"-3.

The synthesis of compounds of Formula I may be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in WO 2007075946, WO 2011019413, WO 2010019239, WO 2007134279, WO 2007079139 and WO 2006002421, the teachings of which are incorporated herein by reference.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I is depicted in Scheme 1. Compounds of Formula I can be prepared wherein each D in the CD3 group has an isotopic enrichment of at least 90% and preferably at least 95%.

Scheme 1:

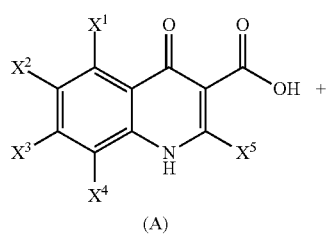

(A)

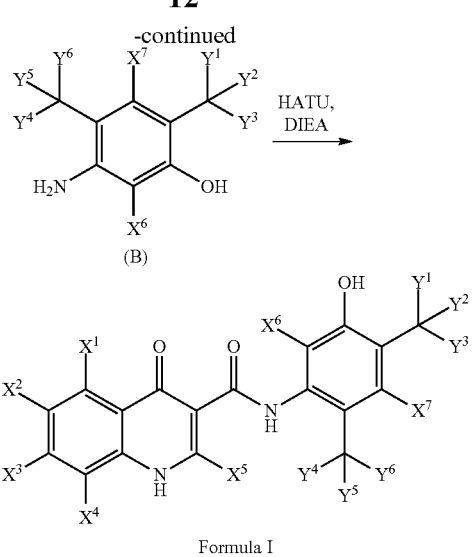

Compounds of Formula I may be prepared as shown in Scheme 1 via the coupling of A and B employing HATU (N,N,N',N'-tetramethyl-O-(7-azabenzotriazol-1-yl)uronium hexafluorophosphate) in the presence of DIEA (N,N'-diisopropylethylamine).

Deuterated intermediates of type A (scheme 1) may be prepared as outlined in scheme 2, analogously to Singh, A.; Van Goor, F.; Worley, F. J. III; Knapp, T. Compounds Useful in CFTR Assays and Methods Therewith WO 2007075946 A1 Jul. 5, 2007, the entire teachings of which are incorporated herein by reference.

Scheme 2:

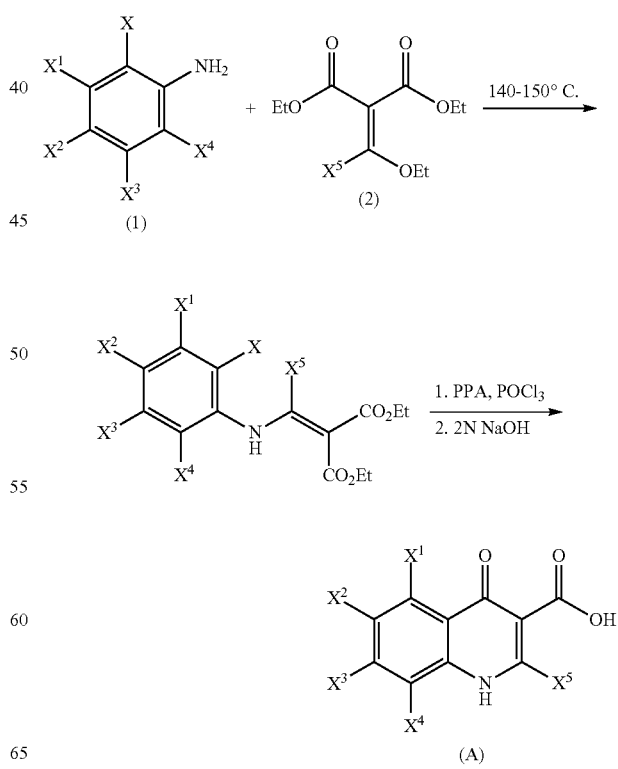

Scheme 2a:

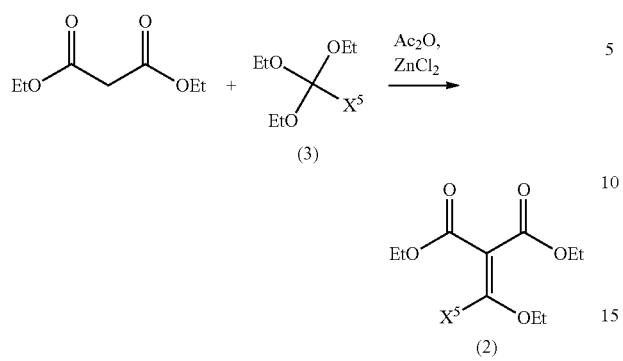

As shown in Scheme 2, heating a mixture of an aniline 1 in the presence of a malonate derivative 2 affords the appropriately deuterated ((phenylamino)methylene)malonate, subsequent exposure of which to polyphosphoric acid in the presence of POCl$_3$ followed by ester hydrolysis provides carboxylic acid A. In Scheme 2, X is hydrogen or deuterium. In one embodiment, X, X$^1$, X$^2$, X$^3$ and X$^4$ are the same.

Exemplary compounds for use in Scheme 2 include the embodiment of compound (1) where X, X$^1$, X$^2$, X$^3$ and X$^4$ are each deuterium, commercially available from Aldrich; and the embodiment of compound (2) where X$^5$ is deuterium, prepared analogously to the procedure described in Scheme 2a (Parham, W. E.; Reed, L. J. Org. Syn., 1948, 28, 60, the teachings of which are incorporated herein by reference) for the case where X$^5$ is hydrogen by employing the embodiment of 3 where X$^5$ is deuterium (available from CDN Isotopes). As shown in Scheme 2a, the appropriately deuterated (ethoxymethylene)malonate of type 2 may be prepared by reaction of diethylmalonate with the appropriately deuterated triethylorthoformate of type 3 in the presence of acetic anhydride and facilitated by ZnCl$_2$.

Deuterated intermediates of type B (Scheme 1) may be prepared as outlined in scheme 3, analogously to Singh, A. et al., supra.

Scheme 3:

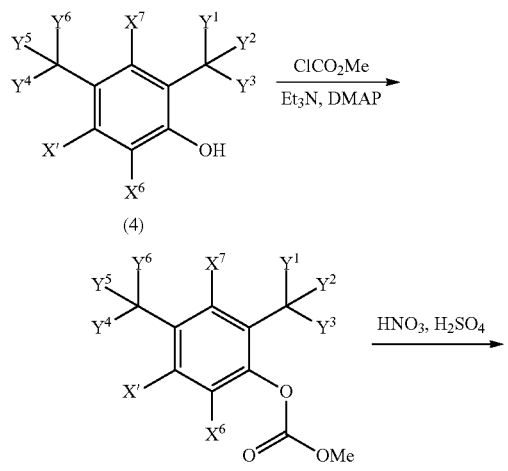

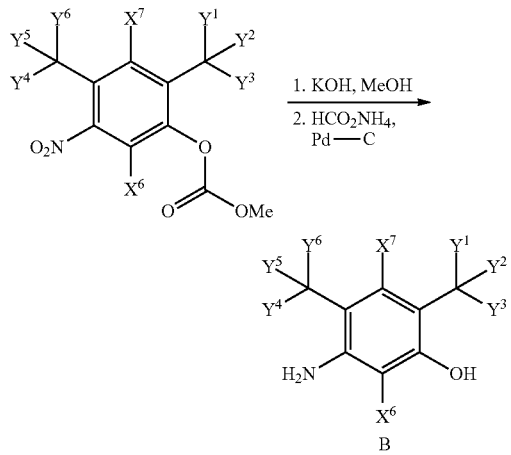

As shown in Scheme 3, protection of di-tertbutylphenols of type 4 with methyl chloroformate followed by exposure to nitric acid results in the formation of a nitro-methylcarbonate intermediate. Subsequent carbonate hydrolysis followed by palladium catalyzed reduction of the nitro group ultimately affords aminophenols of type B. In Scheme 3, X' is hydrogen or deuterium. In one embodiment, X', X$^6$ and X$^7$ are the same.

Compounds of formula B in Scheme 3 may be treated with either DCl or HCl to obtain compounds of formula B', or B", respectively, with a high percentage incorporation of deuterium or hydrogen, respectively, at the X$^6$ position. This procedure is effective regardless of whether X$^6$ in B is hydrogen or deuterium. Thus, if X$^6$ in B is hydrogen, or deuterium at a lower level of isotopic purity than desired, treatment with DCl provides B'; while if X$^6$ is deuterium in B, treatment with HCl provides B". Both treatments are shown in the two equations below:

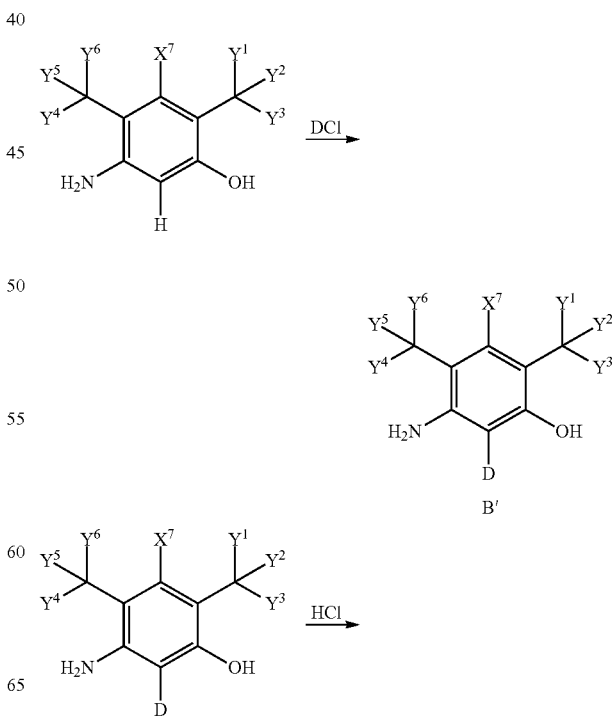

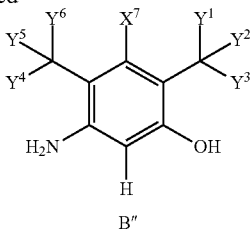

B″

The procedure may be used to exchange H for D, or D for H, and to enrich compounds of formula B having lower levels of isotopic purity (0-85%) at $X^6$. This procedure facilitates the preparation of compounds of formula B′ or B″ containing >95% D or >95% H, respectively, at the position corresponding to $X^6$. B′ or B″ may be then treated with A according to scheme 1 to afford a compound of Formula I wherein $X^6$ is, respectively, deuterium or hydrogen.

Intermediates of the formula B″-1 may analogously be prepared in accordance with the following scheme (where any atom not designated as deuterium is present at its natural isotopic abundance):

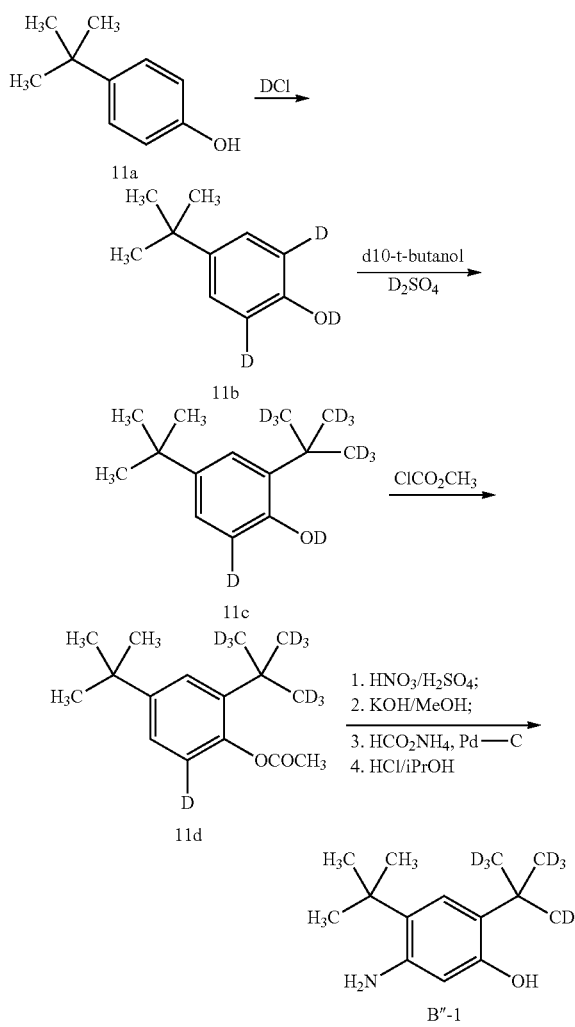

Treatment of 11a with DCl in $D_2O$ at 140° C. efficiently exchanges the ortho hydrogens as well as the phenolic OH with deuterium providing 11b. Exposure of 11b to d10-t-butanol in the presence of $D_2SO_4$ selectively installs the d9-t-butyl moiety at the position ortho to the hydroxyl group affording 11c. Reaction of 11c with methyl chloroformate provides 11d which is then converted to B″-1 via a four step sequence involving nitration, carbonate hydrolysis, nitro reduction and HCl mediated D to H exchange.

Intermediates of the formula B″-2 may analogously be prepared in accordance with the following scheme (where any atom not designated as deuterium is present at its natural isotopic abundance):

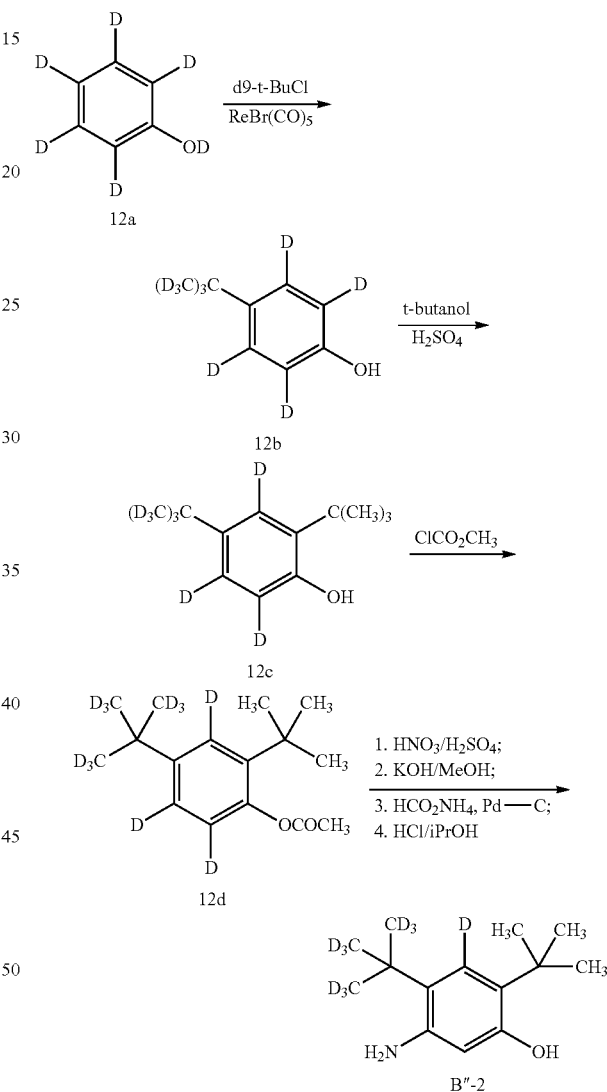

Treatment of 12a with d9-t-butylchloride in the presence of $ReBr(CO)_5$ selectively installs the d9-t-butyl moiety at the position para to the hydroxyl group affording 12b. Exposure of 12b to t-butanol in the presence of $H_2SO_4$ selectively installs the t-butyl moiety at the position ortho to the hydroxyl group affording 12c. Conversion of 12c to B″-2 follows the procedure described above for the conversion of 11c to B″-1.

Intermediates of the formula B″-3 may analogously be prepared in accordance with the following scheme (where any atom not designated as deuterium is present at its natural isotopic abundance):

17

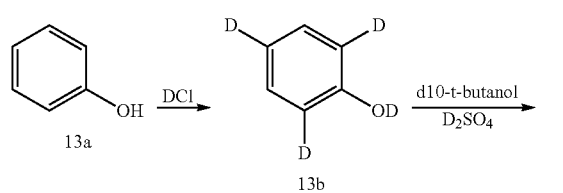
13a → 13b

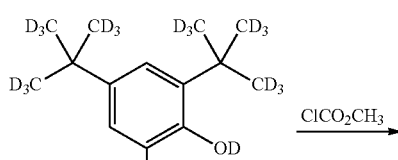
13c

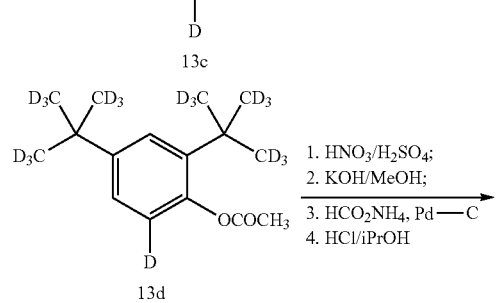
13d

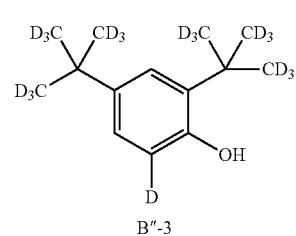
B″-3

Treatment of 13a with DCl in D$_2$O at 140° C. efficiently exchanges the ortho and para hydrogens as well as the phenolic OH with deuterium providing 13b. Exposure of 13b to d10-t-butanol in the presence of D$_2$SO$_4$ selectively installs the d9-t-butyl moieties at the 2 and 4 positions affording 13c. Conversion of 13c to B″-3 follows the procedure described above for the conversion of 11c to B″-1.

B″-1, B″-2 and B″-3 may be respectively converted to the corresponding compounds of formula I by treatment with A analogously to the disclosure of Scheme 1.

Deuterated intermediates of type 4 (Scheme 3) may be prepared as outlined in Schemes 4a-4d, analogously to Sun, Y.; Tang, N. *Huaxue Shiji* 2004, 26, 266-268, the entire teachings of which are incorporated herein by reference.

Scheme 4a:

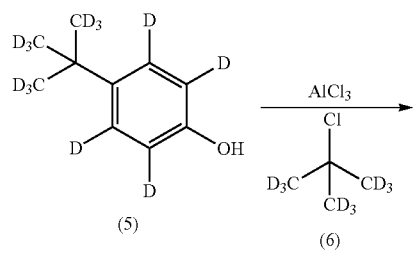

18

-continued

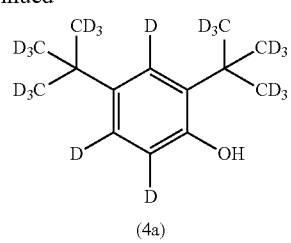
(4a)

Scheme 4b:

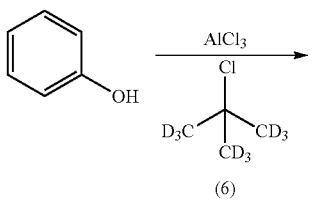

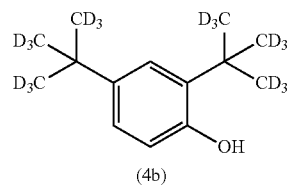
(4b)

Scheme 4c:

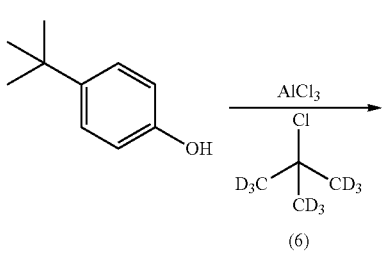

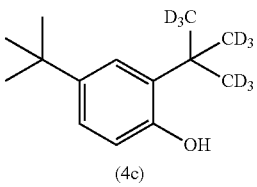
(4c)

Scheme 4d:

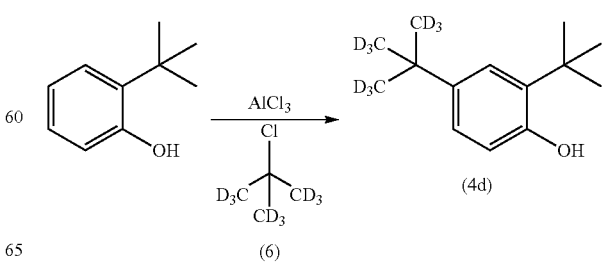
(4d)

As shown in Schemes 4a-4d, ditertbutylphenols of type 4 may be prepared via Friedel-Crafts alkylation of the appropriately deuterated phenol (phenol, 4-tert-butyl phenol or 2-tert butylphenol) with d9-tert butylchloride. The embodiments of compound (4) that may be obtained as shown in scheme 4 are exemplary compounds for use in Scheme 3. In the embodiments 4a, 4b, 4c, and 4d in Scheme 4, any atom not designated as deuterium is present at its natural isotopic abundance. In Scheme 4, both Compound 5 and compound 6 are commercially available (CDN Isotopes).

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, $3^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

In another embodiment, a composition of this invention further comprises a second therapeutic agent. The second therapeutic agent may be selected from any compound or therapeutic agent known to have or that demonstrates advantageous properties when administered with a compound having the same mechanism of action as VX-770.

Preferably, the second therapeutic agent is an agent useful in the treatment of a variety of conditions, including cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear palsy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

In one embodiment, the second therapeutic agent is an agent useful in the treatment of cystic fibrosis.

In one embodiment, the second therapeutic agent is an agent useful in the treatment of COPD.

In one embodiment, the second therapeutic agent is an agent useful in the treatment of Parkinson's disease.

In one embodiment, the second therapeutic agent is an agent useful in the treatment of a bile duct disorder or a kidney ion channel disorder, including, but not limited to, Bartter's syndrome and Dent's disease.

In one embodiment, the second therapeutic agent is VX-809 (lumacaftor) or VX-661.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 0.02 to 2500 mg per treatment. In more specific embodiments the range is from about 0.2 to 1250 mg or from about 0.4 to 500 mg or most specifically from 2 to 250 mg per treatment. Treatment typically is administered one to two times daily. In one embodiment, the compound of the invention is administered two times daily in an amount between 50 and 300 mg each time. In one embodiment, the compound of the invention is administered once daily in an amount between 100 to 500 mg. In the foregoing embodiments, the compound is administered optionally in combination with a second agent. Examples of second agents include CFTR correctors, such as lumacaftor or VX-661. In some embodiments wherein the compound is administered optionally in combination with a second agent, the amount of compound is administered twice daily at between 100 mg and 300 mg each time, such as between 150 mg and 250 mg each time. In other embodiments wherein the compound is administered optionally in combination with a second agent, the amount of compound is administered three times daily at between 100 mg and 300 mg each time, such as between 150 mg and 250 mg each time.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of potentiating the activity of CFTR in an infected cell, comprising contacting such a cell with a compound of Formula I herein, or a pharmaceutically acceptable salt thereof.

According to another embodiment, the invention provides a method of treating a disease that is beneficially treated by VX-770 in a subject in need thereof, comprising the step of administering to the subject an effective amount of a compound or a composition of this invention. In one embodiment the subject is a patient in need of such treatment. Such diseases include cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear palsy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

In one embodiment, a compound of this invention is used to treat cystic fibrosis in a subject such as a patient in need thereof. In one embodiment, a compound of this invention is used to treat COPD in a subject such as a patient in need thereof. In an example of either of the foregoing embodiments, the compound is administered by nasal aerosol or inhalation. In another example of either of the foregoing embodiments, the compound is administered orally.

In one embodiment, a compound of this invention is used to treat Parkinson's Disease in a subject such as a patient in need thereof.

In one embodiment, a compound of this invention is used to treat a bile duct disorder or a kidney ion channel disorder, including, but not limited to, Bartter's syndrome and Dent's disease in a subject such as a patient in need thereof.

In another embodiment, any of the above methods of treatment comprises the further step of co-administering to the subject in need thereof one or more second therapeutic agents. The choice of second therapeutic agent may be made from any second therapeutic agent known to be useful for co-administration with VX-770. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or a pharmaceutically acceptable salt thereof and a second therapeutic agent such as VX-809 (lumacaftor) or VX-661, to a subject in need thereof for treatment.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized Other potential advantages (including without limitation improved dosing regimens and/or reduced drug cost) will be apparent to those of skill in the art.

In yet another aspect, the invention provides the use of a compound of Formula I, or a pharmaceutically acceptable salt thereof, alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I, or a pharmaceutically acceptable salt thereof, for use in the treatment or prevention in a subject of a disease, disorder or symptom thereof delineated herein.

EXAMPLES

Example 1

Synthesis of N-(2,4-Di-(tert-butyl-$d_9$)-3,6-$d_2$-5-hydroxyphenyl)-4-oxo-1,4-dihydroquinoline-3-carboxamide (Compound 110)

Compound 110 was prepared as outlined in Scheme 5 below.

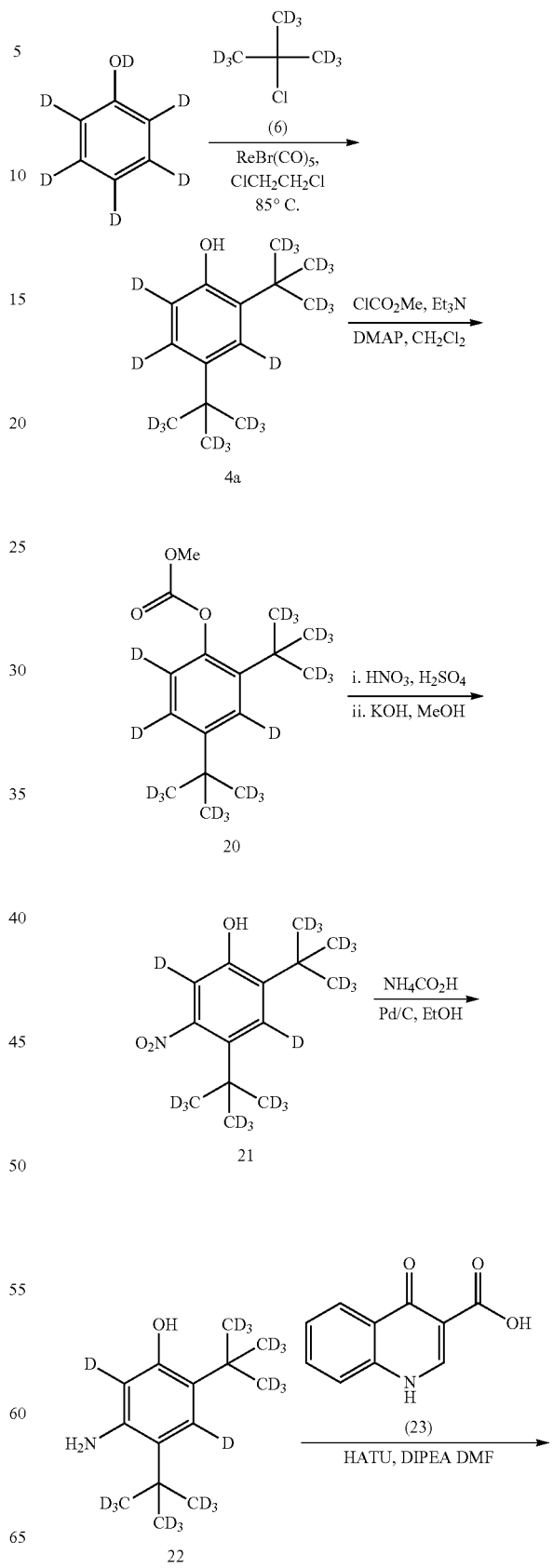

-continued

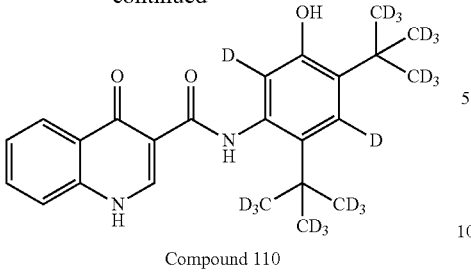

Compound 110

Step 1. 2,4-Di-(tert-butyl-d$_9$)-3,5,6-d$_3$-phenol (4a)

Intermediate 4a was prepared according to the procedure described for the synthesis for 2,4-di-tert-butyl-3,5-d$_2$-phenol employing tert-butyl chloride-d$_9$ in place of tert-butyl-chloride (Kurahashi, T.; Hada, M.; Fujii, H. *J. Am. Chem. Soc.* 2009, 131, 12394-12405): To a solution of phenol-d$_6$ (459 mg, 4.59 mmol, 99 atom % D, Sigma Aldrich) and tert-butyl chloride-d$_9$ (2.50 mL, 23.0 mmol, 98 atom % D, Cambridge Isotope Laboratories, Inc.) in 1,2-dichloroethane (10.0 mL) was added ReBr(CO)$_5$ (19.0 mg, 0.0459 mmol). The reaction mixture was stirred at 85° C. for 15 hours at which time additional tert-butyl chloride-d$_9$ (2.50 mL, 23.0 mmol, 98 atom % D, Cambridge Isotope Laboratories, Inc.) and ReBr(CO)$_5$ (19.0 mg, 0.0459 mmol) was added. Stirring was continued at 85° C. for 2 hours, the mixture was cooled to room temperature, concentrated in vacuo and purified by column chromatography (SiO$_2$, 30% CH$_2$Cl$_2$/heptanes) to afford 4a (0.789 g, 76% yield) as a light yellow oil. MS (ESI) 228.1 [(M+H)$^+$].

Step 2. 2,4-Di-(tert-butyl-d$_9$)-3,5,6-d$_3$-phenyl methyl carbonate (20)

To a solution of 4a (2.72 g, 12.0 mmol), triethylamine (3.33 mL, 23.9 mmol) and N,N-dimethylaminopyridine (73.0 mg, 0.598 mmol) in CH$_2$Cl$_2$ (30.0 mL) at 0° C. was added methyl chloroformate (1.38 mL, 17.9 mmol). The reaction mixture was stirred at room temperature for 15 hours then was diluted with 10% ethyl acetate/heptanes and filtered through a silica plug. The silica plug was then rinsed with additional 10% ethyl acetate/heptanes. The filtrate was combined, and concentrated in vacuo to provide 20 (2.40 g, 70% yield) as a light yellow oil which was carried forward without purification.

Step 3. 2,4-Di-(tert-butyl-d$_9$)-3,6-d$_2$-5-nitrophenol (21)

To a solution of 20 (2.40 g, 8.41 mmol) in sulfuric acid (1.00 mL) at 0° C. was added a 1:1 mixture of sulfuric acid and nitric acid (2.00 mL) dropwise. The reaction mixture was then stirred at room temperature for 2 hours then slowly added to ice water with vigorous stirring. The resulting slurry was extracted with ethyl acetate (3×100 mL) and the combined organic layers were dried (Na$_2$SO$_4$), filtered and concentrated to afford an amber oil containing a mixture of regioisomers. This crude oil was then taken up in MeOH (50 mL) and KOH (1.54 g, 27.5 mmol) was added. The reaction mixture was stirred at room temperature for 2 hours then was acidified to pH=2 with concentrated HCl. The resulting solution was extracted with diethyl ether (3×100 mL), dried (MgSO$_4$), filtered and concentrated. The residue was then purified via column chromatography (SiO$_2$, 0-5% ethyl acetate/heptanes) to afford 21 (526 mg, 23%) as a light yellow solid. MS (ESI) 270.3 [(M–H)$^-$].

Step 4. 5-Amino-2,4-di-(tert-butyl-d$_9$)-3,6-d$_2$-phenol (22)

A solution of 21 (526 mg, 1.94 mmol) and ammonium formate (489 mg, 7.75 mmol) in ethanol (25.0 mL) was heated to the point of reflux. At this time, 10% Pd/C (250 mg, 50% wet) was added in small portions and the reaction mixture was stirred at reflux for 2 hours. The mixture was then cooled to room temperature, diluted with THF, filtered through Celite® and concentrated in vacuo to afford 22 (473 mg, 100%) as a tan solid. MS (ESI) 242.4 [(M+H)$^+$].

Step 5. N-(2,4-Di-(tert-butyl-d$_9$)-3,6-d$_2$-5-hydroxyphenyl)-4-oxo-1,4-dihydroquinoline-3-carboxamide (Compound 110)

To a solution of 22 (250 mg, 1.04 mmol), 4-oxo-1,4-dihydroquinoline-3-carboxylic acid (23, purchased from Matrix Scientific, 98.0 mg, 0.518 mmol) and N,N-diisopropylethylamine (181 μL, 1.04 mmol) in DMF (5.00 mL) was added HATU (197 mg, 0.518 mmol). The reaction mixture was stirred at room temperature for 3 hours then was diluted with saturated NaHCO$_3$ and extracted with ethyl acetate (3×50 mL). The combined organic extracts were washed with water (3×20 mL), dried (Na$_2$SO$_4$), filtered and concentrated in vacuo. The resulting residue was purified via column chromatography (SiO$_2$, 0-70% ethyl acetate/heptanes) to afford Compound 110 (77.0 mg, 36% Yield) as a white solid. $^1$H NMR (d$_6$-DMSO, 400 MHz): δ 12.87 (br s, 1H), 11.80 (s, 1H), 9.18 (s, 1H), 8.86 (s, 1H), 8.32 (d, J=8.2 Hz, 1H), 7.81 (t, J=7.9 Hz, 1H), 7.76 (t, J=8.2 Hz, 1H), 7.51 (t, J=7.4 Hz, 1H), 7.10 (s, 0.2H)*; MS (ESI) 413.5 [(M+H)$^+$]. * The $^1$H NMR signal at 7.10 ppm indicates approximately 80% deuterium incorporation at one of the two deuterated aryl positions. The absence of signals at 7.20 ppm and 1.37 ppm indicate high levels of incorporation (>95%) at the remaining deuterated positions.

Example 2

Synthesis of N-(2-(tert-Butyl)-4-(tert-butyl-d$_9$)-6-d-5-hydroxyphenyl)-4-oxo-1,4-dihydroquinoline-3-carboxamide (Compound 125)

Compound 125 was prepared as outlined in Scheme 6 below.

Scheme 6. Preparation of Compound 125

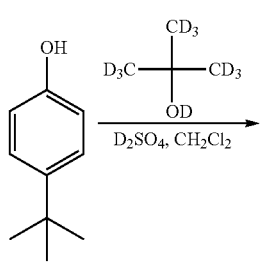

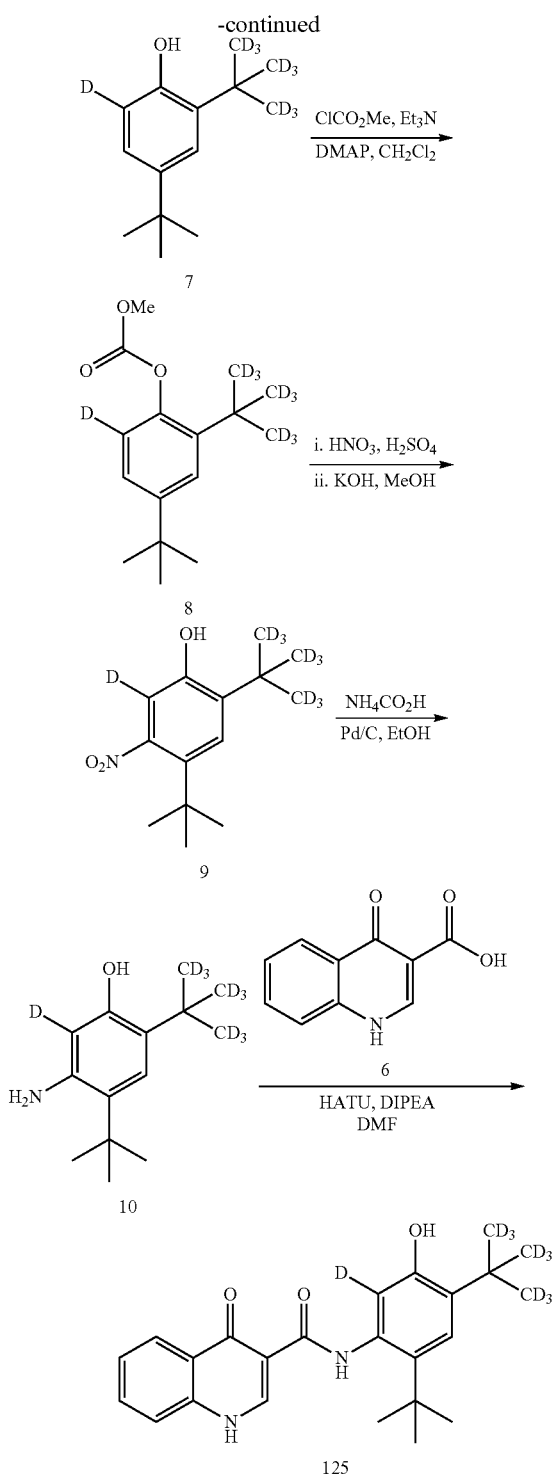

Step 1. 2-(tert-Butyl-$d_9$)-4-(tert-butyl)-6-d-phenol (7)

To a solution of 4-tert-butyl phenol (3.43 g, 22.7 mmol) and tert-butyl alcohol-d10 (3.00 mL, 31.8 mmol, 98 atom % D, Cambridge Isotope Laboratories, Inc.) in dichloromethane (40.0 mL) was added $D_2SO_4$ (1.50 mL, 99.5 atom % D, Sigma-Aldrich). The reaction was stirred at room temperature for 15 hours then was diluted with water and extracted with dichloromethane (3×100 mL). The organic layers were combined, washed with saturated $NaHCO_3$, dried ($Na_2SO_4$), filtered and concentrated in vacuo. The resulting oil was purified by column chromatography ($SiO_2$, 0-15% ethyl acetate/heptanes) to afford 7 (4.04 g, 83% yield) as a clear oil. $^1$H NMR ($d_6$-DMSO, 400 MHz) δ 9.04 (s, 1H), 7.12 (d, J=2.4 Hz, 1H), 6.98 (dd, J=3.8, 2.5 Hz, 1H), 6.67 (d, J=8.3 Hz, 0.3H), 1.22 (s, 10H).

Step 2. 2-(tert-Butyl-$d_9$)-4-(tert-butyl)-6-d-phenyl methyl carbonate (8)

To a solution of 7 (4.04 g, 18.8 mmol), triethylamine (5.24 mL, 37.6 mmol) and N,N-dimethylaminopyridine (115 mg, 0.940 mmol) in $CH_2Cl_2$ (40.0 mL) at 0° C. was added methyl chloroformate (2.17 mL, 28.2 mmol). The reaction was stirred at room temperature for 15 hours and additional triethylamine (1.30 mL, 9.33 mmol) and methyl chloroformate (0.550 mL, 7.15 mmol) were added. After stirring for an additional 1 hour the reaction was diluted with 10% ethyl acetate/heptanes and filtered through a silica plug. The silica plug was then rinsed with additional 10% ethyl acetate/heptanes. The filtrate was combined and concentrated in vacuo to provide 8 (4.69 g, 91% yield) as a light yellow oil which was carried forward without purification. $^1$H NMR ($d_6$-DMSO, 400 MHz) δ 7.33 (d, J=2.4 Hz, 1H), 7.30-7.20 (m, 1H), 7.06 (d, J=8.5 Hz, 0.3H), 3.84 (d, J=0.7 Hz, 3H), 1.28 (s, 9H).

Step 3. 2-(tert-Butyl-$d_9$)-4-(tert-butyl)-6-d-5-nitrophenol (9)

To a solution of 8 (4.69 g, 17.2 mmol) in sulfuric acid (2.00 mL) at 0° C. was added a 1:1 mixture of sulfuric acid and nitric acid (4.00 mL) dropwise. The reaction was then stirred at room temperature for two hours then slowly added to ice water with vigorous stirring. The resulting slurry was extracted with ethyl acetate (3×100 mL) and the combined organic layers were dried ($Na_2SO_4$), filtered and concentrated to afford an amber oil containing a mixture of regio-isomers. This crude oil was then taken up in MeOH (100 mL) and KOH (3.50 g) was added. The reaction stirred at room temperature for 2 hours then was acidified to pH=2 with concentrated HCl. The resulting solution was extracted with diethyl ether (3×100 mL), dried ($MgSO_4$), filtered and concentrated. The residue was then purified via column chromatography ($SiO_2$, 0-5% ethyl acetate/heptanes) to afford 9 (1.33 g, 30%) as a light yellow solid. MS (ESI) 260.2 [(M−H)$^−$].

Step 4. 5-Amino-2-(tert-butyl-$d_9$)-4-(tert-butyl)-6-d-phenol (10)

A solution of 9 (1.33 g, 5.11 mmol) and ammonium formate (1.29 g, 20.4 mmol) in ethanol (60.0 mL) was heated to reflux. At this time, 10% Pd/C (650 mg, 50% wet) was added in small portions and the reaction continued to stir at reflux for two hours. The reaction was then cooled to room temperature, diluted with THF, filtered through Celite® and concentrated in vacuo to afford 10 (1.19 g, 100%) as a pink solid. MS (ESI) 232.3 [(M+H)$^+$].

Step 5. N-(2-(tert-Butyl)-4-(tert-butyl-$d_9$)-6-d-5-hydroxyphenyl)-4-oxo-1,4-dihydroquinoline-3-carboxamide (125)

To a solution of 10 (892 mg, 3.87 mmol), 4-oxo-1,4-dihydroquinoline-3-carboxylic acid (11, purchased from Matrix Scientific, 366 mg, 1.93 mmol) and N,N-diisopropylethylamine (674 μL, 3.87 mmol) in DMF (20.0 mL) was added HATU (734 mg, 1.93 mmol). The reaction was stirred at room temperature for three hours then was diluted with saturated NaHCO$_3$ and extracted with ethyl acetate (3×50 mL). The combined organic extracts were washed with water (3×20 mL), dried (Na$_2$SO$_4$), filtered and concentrated in vacuo. The resulting residue was purified via column chromatography (SiO$_2$, 0-70% ethyl acetate/heptanes) to afford 125 (277 mg, 36% Yield) as a white solid. $^1$H NMR (d$_6$-DMSO, 400 MHz) δ 12.88 (s, 1H), 11.81 (s, 1H), 9.19 (s, 1H), 8.86 (s, 1H), 8.32 (dd, J=8.1, 1.4 Hz, 1H), 7.86-7.77 (m, 1H), 7.75 (d, J=8.2 Hz, 1H), 7.51 (s, 1H), 7.15 (s, 1H), 7.09 (s, 0.3H)*, 1.37 (s, 9H), MS (ESI) 403.3 [(M+H)$^+$]. * The 1H NMR signal at 7.09 ppm indicates approximately 70% deuterium incorporation at one of the two aryl positions.

Example 3

Synthesis of N-(2-(tert-Butyl)-4-(tert-butyl-d$_9$)-5-hydroxyphenyl)-4-oxo-1,4-dihydroquinoline-3-carboxamide (Compound 106)

Compound 106 was prepared as outlined in Scheme 7 below.

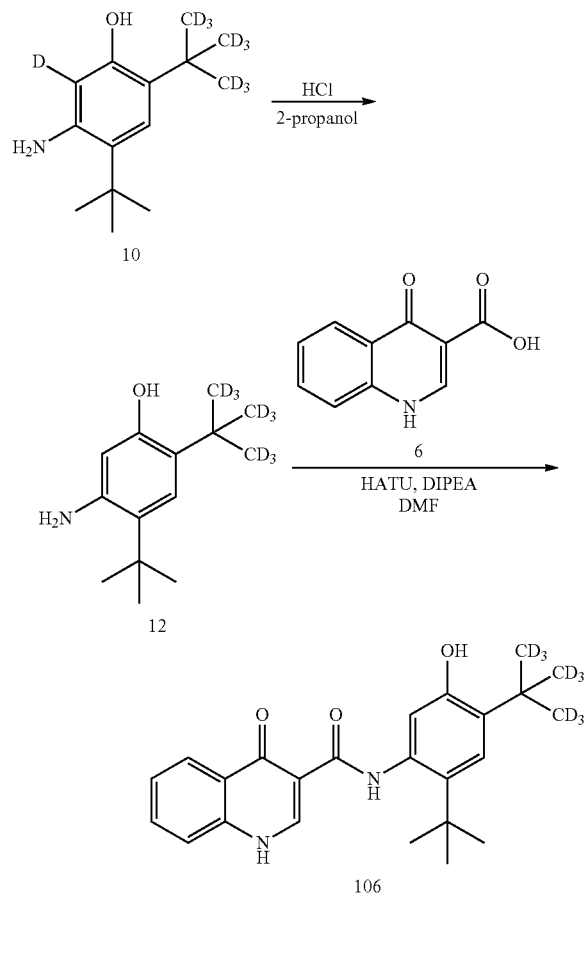

Step 1. 5-Amino-2-(tert-butyl-d$_9$)-4-(tert-butyl)-phenol (12)

Compound 10 (298 mg, 1.29 mmol), prepared as disclosed in Example 2, was dissolved in 5M HCl in 2-propanol (20 mL) and the reaction was stirred at room temperature for 15 hours. The reaction was then concentrated in vacuo and taken back up in 5M HCl in 2-propanol (20 mL). After stirring for an additional 15 hours at room temperature, the reaction was concentrated in vacuo and diluted with saturated aqueous sodium bicarbonate (100 mL). The resulting aqueous solution was extracted with dichloromethane (3×50 mL). The organic layers were combined, dried (Na$_2$SO$_4$), filtered and concentrated in vacuo to afford 12 (240 mg, 81%) as a pink solid. $^1$H NMR (d6-DMSO, 400 MHz) δ 8.62 (s, 1H), 6.83 (s, 1H), 6.08 (s, 1H), 1.27 (s, 9H).

Step 2. N-(2-(tert-Butyl)-4-(tert-butyl-d$_9$)-5-hydroxyphenyl)-4-oxo-1,4-dihydroquinoline-3-carboxamide (106)

To a solution of 12 (240 mg, 1.04 mmol), 4-oxo-1,4-dihydroquinoline-3-carboxylic acid (11, purchased from Matrix Scientific, 99 mg, 0.521 mmol) and N,N-diisopropylethylamine (181 µL, 1.04 mmol) in DMF (6.00 mL) was added HATU (198 mg, 0.521 mmol). The reaction was stirred at room temperature for three hours then was diluted with saturated NaHCO$_3$ and extracted with ethyl acetate (3×50 mL). The combined organic extracts were washed with water (3×20 mL), dried (Na$_2$SO$_4$), filtered and concentrated in vacuo. The resulting residue was purified via column chromatography (SiO$_2$, 0-70% ethyl acetate/heptanes) to afford 106 (80 mg, 38% Yield) as a white solid. $^1$H NMR (d$_6$-DMSO, 400 MHz) δ 12.88 (s, 1H), 11.81 (s, 1H), 9.19 (s, 1H), 8.86 (s, 1H), 8.32 (dd, J=8.1, 1.4 Hz, 1H), 7.86-7.77 (m, 1H), 7.75 (d, J=8.2 Hz, 1H), 7.51 (s, 1H), 7.15 (s, 1H), 7.09 (s, 1H), 1.37 (s, 9H); MS (ESI) 402.3 [(M+H)$^+$].

In one batch run, the isotopic enrichment factor for X$^7$ in 106 was found to be about 466.7 (7% deuterium incorporation). In one batch run, the isotopic enrichment factor for X$^7$ in 106 was found to be about 733.3 (11% deuterium incorporation).

Example 4

Synthesis of N-(2,4-Di-(tert-butyl-d$_9$)-5-hydroxyphenyl)-4-oxo-1,4-dihydroquinoline-3-carboxamide (Compound 105)

Compound 105 was prepared as outlined in Scheme 5 below.

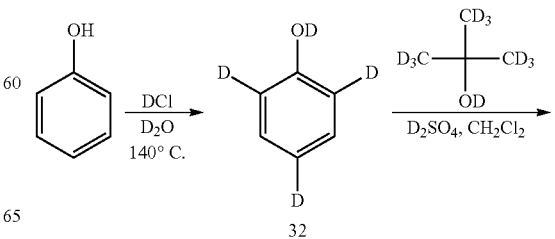

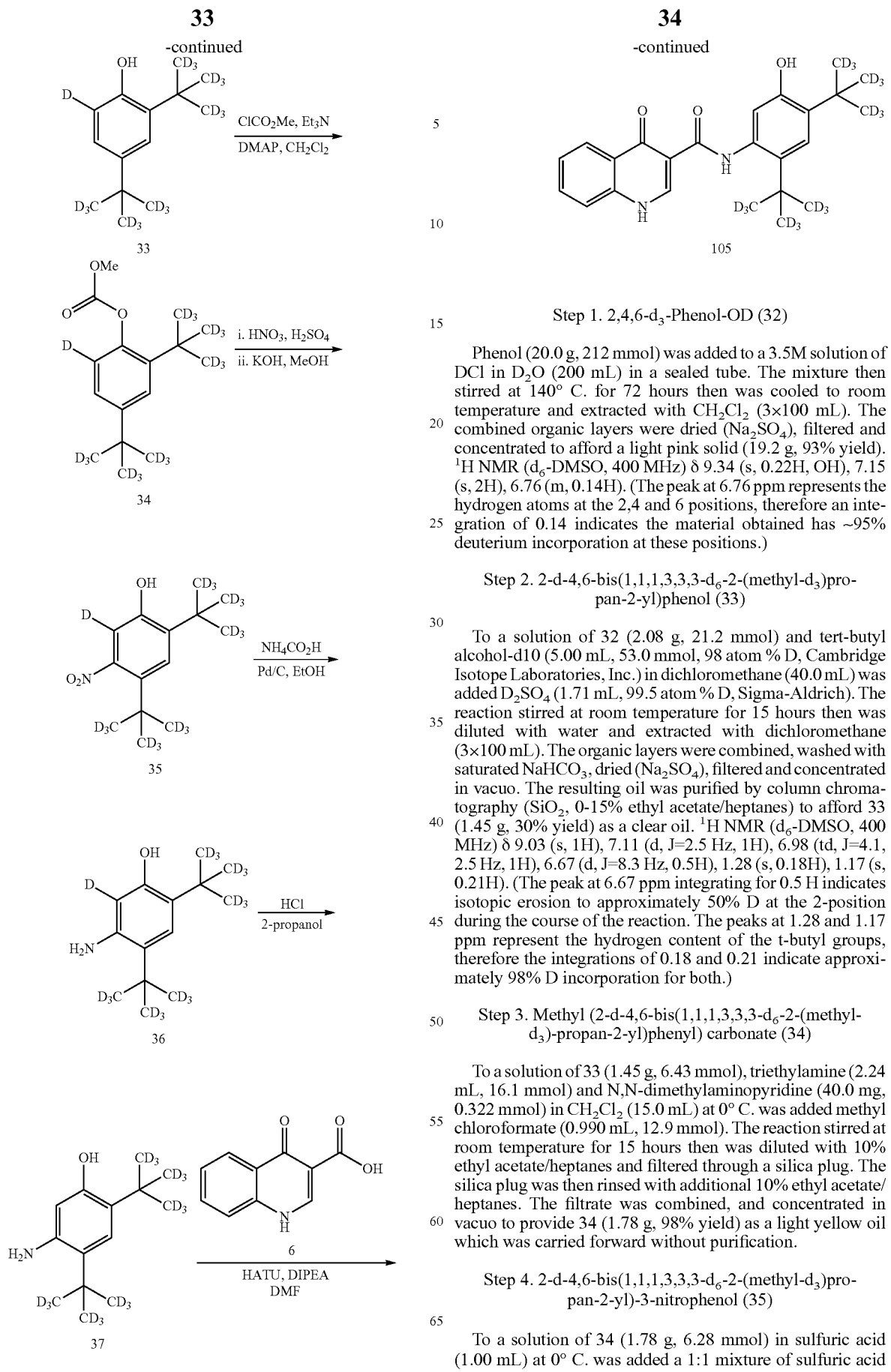

Step 1. 2,4,6-d$_3$-Phenol-OD (32)

Phenol (20.0 g, 212 mmol) was added to a 3.5M solution of DCl in D$_2$O (200 mL) in a sealed tube. The mixture then stirred at 140° C. for 72 hours then was cooled to room temperature and extracted with CH$_2$Cl$_2$ (3×100 mL). The combined organic layers were dried (Na$_2$SO$_4$), filtered and concentrated to afford a light pink solid (19.2 g, 93% yield). $^1$H NMR (d$_6$-DMSO, 400 MHz) δ 9.34 (s, 0.22H, OH), 7.15 (s, 2H), 6.76 (m, 0.14H). (The peak at 6.76 ppm represents the hydrogen atoms at the 2,4 and 6 positions, therefore an integration of 0.14 indicates the material obtained has ~95% deuterium incorporation at these positions.)

Step 2. 2-d-4,6-bis(1,1,1,3,3,3-d$_6$-2-(methyl-d$_3$)propan-2-yl)phenol (33)

To a solution of 32 (2.08 g, 21.2 mmol) and tert-butyl alcohol-d10 (5.00 mL, 53.0 mmol, 98 atom % D, Cambridge Isotope Laboratories, Inc.) in dichloromethane (40.0 mL) was added D$_2$SO$_4$ (1.71 mL, 99.5 atom % D, Sigma-Aldrich). The reaction stirred at room temperature for 15 hours then was diluted with water and extracted with dichloromethane (3×100 mL). The organic layers were combined, washed with saturated NaHCO$_3$, dried (Na$_2$SO$_4$), filtered and concentrated in vacuo. The resulting oil was purified by column chromatography (SiO$_2$, 0-15% ethyl acetate/heptanes) to afford 33 (1.45 g, 30% yield) as a clear oil. $^1$H NMR (d$_6$-DMSO, 400 MHz) δ 9.03 (s, 1H), 7.11 (d, J=2.5 Hz, 1H), 6.98 (td, J=4.1, 2.5 Hz, 1H), 6.67 (d, J=8.3 Hz, 0.5H), 1.28 (s, 0.18H), 1.17 (s, 0.21H). (The peak at 6.67 ppm integrating for 0.5 H indicates isotopic erosion to approximately 50% D at the 2-position during the course of the reaction. The peaks at 1.28 and 1.17 ppm represent the hydrogen content of the t-butyl groups, therefore the integrations of 0.18 and 0.21 indicate approximately 98% D incorporation for both.)

Step 3. Methyl (2-d-4,6-bis(1,1,1,3,3,3-d$_6$-2-(methyl-d$_3$)-propan-2-yl)phenyl) carbonate (34)

To a solution of 33 (1.45 g, 6.43 mmol), triethylamine (2.24 mL, 16.1 mmol) and N,N-dimethylaminopyridine (40.0 mg, 0.322 mmol) in CH$_2$Cl$_2$ (15.0 mL) at 0° C. was added methyl chloroformate (0.990 mL, 12.9 mmol). The reaction stirred at room temperature for 15 hours then was diluted with 10% ethyl acetate/heptanes and filtered through a silica plug. The silica plug was then rinsed with additional 10% ethyl acetate/heptanes. The filtrate was combined, and concentrated in vacuo to provide 34 (1.78 g, 98% yield) as a light yellow oil which was carried forward without purification.

Step 4. 2-d-4,6-bis(1,1,1,3,3,3-d$_6$-2-(methyl-d$_3$)propan-2-yl)-3-nitrophenol (35)

To a solution of 34 (1.78 g, 6.28 mmol) in sulfuric acid (1.00 mL) at 0° C. was added a 1:1 mixture of sulfuric acid and nitric acid (2.00 mL) dropwise. The reaction was then stirred at room temperature for two hours then slowly added to ice water with vigorous stirring. The resulting slurry was extracted with ethyl acetate (3×100 mL) and the combined organic layers were dried (Na$_2$SO$_4$), filtered and concentrated to afford an amber oil containing a mixture of regioisomers. This crude oil was then taken up in MeOH (20 mL) and KOH (664 mg, 11.8 mmol) was added. The reaction stirred at room temperature for 2 hours then was acidified to pH=2 with concentrated HCl. The resulting solution was extracted with diethyl ether (3×100 mL), dried (MgSO$_4$), filtered and concentrated. The residue was then purified via column chromatography (SiO$_2$, 0-5% ethyl acetate/heptanes) to afford 35 (319 mg, 19%) as a light yellow solid. MS (ESI) 269.3 [(M−H)$^+$].

Step 5. 3-Amino-2-d-4,6-bis(1,1,1,3,3,3-d$_6$-2-(methyl-d$_3$)propan-2-yl)phenol (36)

A solution of 35 (319 mg, 1.18 mmol) and ammonium formate (298 mg, 4.72 mmol) in ethanol (20.0 mL) was heated to reflux. At this time, 10% Pd/C (160 mg, 50% wet) was added in small portions and the reaction continued to stir at reflux for two hours. The reaction was then cooled to room temperature, diluted with THF and filtered through Celite® and concentrated in vacuo to afford 36 (279 mg, 98%) as a tan solid. MS (ESI) 241.3 [(M+H)$^+$].

Step 6. 3-Amino-4,6-bis(1,1,1,3,3,3-d$_6$-2-(methyl-d$_3$)propan-2-yl)phenol (37)

Compound 36 (279 mg, 1.16 mmol) was dissolved in 5M HCl in 2-propanol (20 mL) and the reaction stirred at room temperature for 15 hours. The reaction was then concentrated in vacuo and taken back up in 5M HCl in 2-propanol (20 mL). After stirring for an additional 15 hours at room temperature, the reaction was concentrated in vacuo and diluted with saturated aqueous sodium bicarbonate (100 mL). The resulting aqueous solution was extracted with dichloromethane (3×50 mL). The organic layers were combined, dried (Na$_2$SO$_4$), filtered and concentrated in vacuo to afford 37 (255 mg, 91%) as a pink solid. MS (ESI) 240.3 [(M+H)$^+$].

Step 7. N-(2,4-Di-(tert-butyl-d$_9$)-5-hydroxyphenyl)-4-oxo-1,4-dihydroquinoline-3-carboxamide (105)

To a solution of 37 (255 mg, 1.06 mmol), 4-oxo-1,4-dihydroquinoline-3-carboxylic acid (purchased from Matrix Scientific, 100 mg, 0.532 mmol) and N,N-diisopropylethylamine (185 µL, 1.06 mmol) in DMF (6.00 mL) was added HATU (202 mg, 0.532 mmol). The reaction stirred at room temperature for three hours then was diluted with saturated NaHCO$_3$ and extracted with ethyl acetate (3×50 mL). The combined organic extracts were washed with water (3×20 mL), dried (Na$_2$SO$_4$), filtered and concentrated in vacuo. The resulting residue was purified via column chromatography (SiO$_2$, 0-70% ethyl acetate/heptanes) to afford 105 (92 mg, 42% yield) as a white solid. $^1$H NMR (d$_6$-DMSO, 400 MHz) δ 12.88 (s, 1H), 11.81 (s, 1H), 9.19 (s, 1H), 8.86 (s, 1H), 8.32 (dd, J=8.1, 1.5 Hz, 1H), 7.86-7.69 (m, 2H), 7.51 (ddd, J=8.2, 6.7, 1.4 Hz, 1H), 7.14 (s, 1H), 7.10 (s, 1H), 1.32 (s, 0.2H), 1.30 (s, 0.18H). (The peaks at 1.32 and 1.30 ppm represent the hydrogen content of the t-butyl groups, therefore the integrations of 0.20 and 0.18 indicate approximately 98% D incorporation for both.) MS (ESI) 411.4 [(M+H)$^+$].

In one batch run, the isotopic enrichment factor for X$^7$ in 105 was found to be about 266.7 (4% deuterium incorporation). In one batch run, the isotopic enrichment factor for X$^7$ in 105 was found to be about 333.3 (5% deuterium incorporation).

Example 5

Synthesis of N-(2-(tert-Butyl-d$_9$)-4-(tert-butyl)-3-d-5-hydroxyphenyl)-4-oxo-1,4-dihydroquinoline-3-carboxamide (Compound 123)

Compound 123 was prepared as outlined in Scheme 6 below.

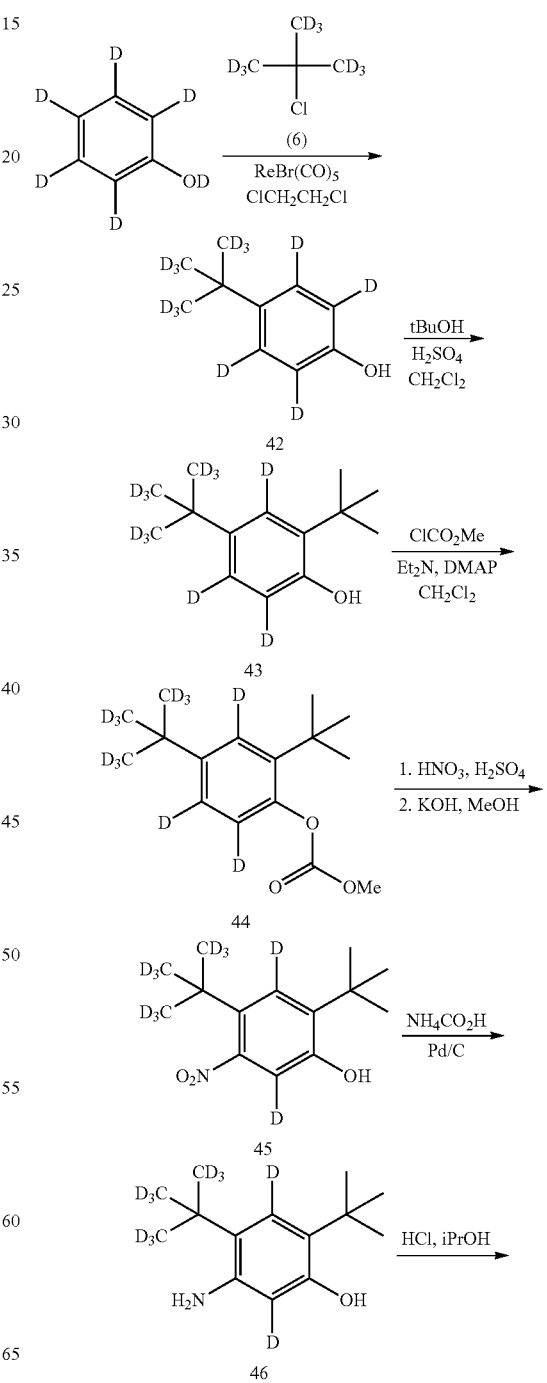

-continued

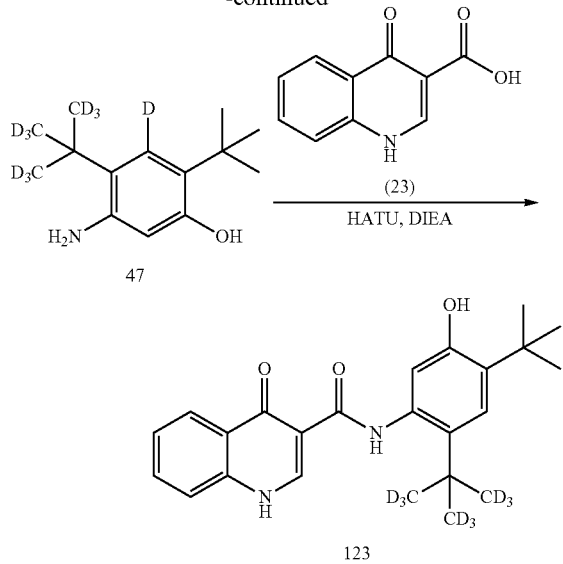

Step 1. 4-tert-butylphenol-d$_{13}$ (42)

To a solution of phenol-d6 (2.06 g, 20.6 mmol, 99 atom % D, Sigma-Aldrich) and tert-butyl chloride-d9 (6.73 mL, 61.8 mmol, 98 atom % D, Cambridge Isotope Laboratories, Inc.) in 1,2-dichloroethane (40.0 mL) was added ReBr(CO)$_5$ (84.0 mg, 0.210 mmol). The reaction stirred at 80° C. for 15 hours at which time the reaction was cooled to room temperature, concentrated in vacuo and purified by column chromatography (SiO$_2$, 0-10% EtOAc/heptanes) to afford 42 (1.95 g, 58% yield) as a colorless crystalline solid. MS (ESI) 162.1[(M–H)$^+$].

Step 2. 2-(tert-Butyl)-3,5,6-d$_3$-4-(tert-butyl-d$_9$)-phenol (43)

To a solution of 42 (1.95 g, 12.0 mmol) and tert-butyl alcohol-d10 (1.60 mL, 16.7 mmol, 98 atom % D, Cambridge Isotope Laboratories, Inc.) in dichloromethane (30 mL) was added D$_2$SO$_4$ (0.900 mL, 99.5 atom % D, Sigma-Aldrich). The reaction stirred at room temperature for 15 hours then was diluted with water and extracted with dichloromethane (3×100 mL). The organic layers were combined, washed with saturated NaHCO$_3$, dried (Na$_2$SO$_4$), filtered and concentrated in vacuo. The resulting oil was purified by column chromatography (SiO$_2$, 0-15% ethyl acetate/heptanes) to afford 43 (782 mg, 30% yield) as a clear oil.

Step 3. 2-(tert-Butyl)-3,5,6-d$_3$-4-(tert-butyl-d$_9$)phenyl methyl carbonate (44)

To a solution of 43 (782 mg, 3.59 mmol), triethylamine (1.25 mL, 8.98 mmol) and N,N-dimethylaminopyridine (22.0 mg, 0.180 mmol) in DCM (10.0 mL) at 0° C. was added a solution of methyl chloroformate (0.552 mL, 7.17 mmol) in DCM (2.00 mL) dropwise over 30 minutes. The reaction stirred at room temperature for 2 hours then was diluted with 20% ethyl acetate/heptanes (50.0 mL) and filtered through a silica plug. The silica plug was then rinsed with additional 20% ethyl acetate/heptanes (3×50 mL). The filtrate was combined, and concentrated in vacuo to provide 44 (930 mg, 94% yield) as a light yellow oil which was carried forward without purification.

Step 4. 2-(tert-Butyl)-3,6-d$_2$-4-(tert-butyl-d$_9$)-5-nitrophenol (45)

To a solution of 44 (0.930 g, 3.36 mmol) in sulfuric acid (0.500 mL) at 0° C. was added a 1:1 mixture of sulfuric acid and nitric acid (1.00 mL) dropwise. The reaction was then stirred at room temperature for two hours then slowly added to ice water with vigorous stirring. The resulting slurry was extracted with diethyl ether (3×50 mL) and the combined organic layers were dried (Na$_2$SO$_4$), filtered and concentrated. The resulting oil was purified via column chromatography (SiO$_2$, 0-10% EtOAc/heptanes) to afford the nitrophenyl methyl carbonate as a mixture of 2 regioisomers. The mixture of regioisomers was then taken up in MeOH (5.00 mL) and KOH (205 mg, 3.66 mmol) was added. The reaction stirred at room temperature for 2 hours then was diluted with 1N HCl. The resulting solution was extracted with DCM (3×25 mL), dried (Na$_2$SO$_4$), filtered and concentrated. The resulting orange solid was then slurried in hexane (25.0 mL) at 0° C. for 20 minutes. The solids were then collected by filtration, washed with additional cold hexane, and dried to afford 45 (52.0 mg, 19% yield) as a light yellow solid. MS (ESI) 260.2 [(M–H)$^+$].

Step 5. 5-Amino-2-(tert-butyl)-3,6-d$_2$-4-(tert-butyl-d$_9$)-phenol (46)

A solution of 45 (52.0 mg, 0.199 mmol) and ammonium formate (50.0 mg, 0.796 mmol) in ethanol (5.00 mL) was heated to reflux. At this time, 10% Pd/C (25.0 mg, 50% wet) was added in small portions and the reaction continued to stir at reflux for two hours. The reaction was then cooled to room temperature, diluted with THF and filtered through Celite® and concentrated in vacuo to afford 46 (46.0 mg, 100%) as a tan solid. MS (ESI) 233.4 [(M+H)$^+$].

Step 6. 5-Amino-2-(tert-butyl)-5-d-4-(tert-butyl-d$_9$)-phenol (47)

Compound 46 (46.0 mg, 0.198 mmol) was dissolved in 5M HCl in 2-propanol (10 mL) and the reaction stirred at room temperature for 15 hours. The reaction was then concentrated in vacuo and re-dissolved in 5M HCl in 2-propanol (10 mL). After stirring for an additional 15 hours at room temperature, the reaction was concentrated in vacuo and diluted with saturated aqueous sodium bicarbonate (50 mL). The resulting aqueous solution was extracted with dichloromethane (3×50 mL). The organic layers were combined, dried (Na$_2$SO$_4$), filtered and concentrated in vacuo to afford 47 (42.0 mg, 91%) as a pink solid. MS (ESI) 232.3 [(M+H)$^+$].

Step 7. N-(2-(tert-Butyl-d$_9$)-4-(tert-butyl)-3-d-5-hydroxyphenyl)-4-oxo-1,4-dihydroquinoline-3-carboxamide (123)

To a solution of 47 (40.0 mg, 0.173 mmol), 4-oxo-1,4-dihydroquinoline-3-carboxylic acid (purchased from Matrix Scientific, 16.0 mg, 0.0870 mmol) and N,N-diisopropylethylamine (30.0 µL, 0.173 mmol) in DMF (2.00 mL) was added HATU (33.0 mg, 0.0870 mmol). The reaction stirred at room temperature for three hours then was diluted with saturated NaHCO$_3$ and extracted with ethyl acetate (3×50 mL). The combined organic extracts were washed with water (3×20 mL), dried (Na$_2$SO$_4$), filtered and concentrated in vacuo. The resulting residue was purified via column chromatography (SiO$_2$, 0-70% ethyl acetate/heptanes) and dried in a vacuum oven at 50° C. to afford 123 (11.0 mg, 31% yield) as a white solid. $^1$H NMR (d$_6$-DMSO, 400 MHz) δ 12.88 (s, 1H), 11.81 (s, 1H), 9.20 (s, 1H), 8.86 (s, 1H), 8.32 (dd, J=8.2, 1.4 Hz, 1H), 7.86-7.71 (m, 2H), 7.51 (ddd, J=8.2, 6.8, 1.3 Hz, 1H), 7.10 (s, 1H), 1.32 (s, 0.2H), 1.36 (s, 9.18H). (The peak at 1.36 represents the combined hydrogen content of the t-butyl groups. Therefore, if we assume the ortho t-butyl group is 100% H, the total integration of 9.18 indicates the para t-butyl is integrating 0.18, which corresponds to approximately 2% H or approximately 98% D.) MS (ESI) 403.3 [(M+H)$^+$].

Example 6a

Evaluation of Metabolic Stability of Compound 110—Human CYP3A4 Supersomes™

Supersomes™ Assay.

7.5 mM stock solutions of test compounds, Compound 110 and ivacaftor, were prepared in DMSO. The 7.5 mM stock solutions were diluted to 50 mM in acetonitrile (ACN). Human CYP3A4 Supersomes™ (1000 pmol/mL, purchased from BD Gentest™ Products and Services) were diluted to 62.5 pmol/mL in 0.1 M potassium phosphate buffer, pH 7.4, containing 3 mM MgCl$_2$. The diluted supersomes were added to wells of a 96-well polypropylene plate in triplicate. A 10 mL aliquot of the 50 mM test compound was added to the supersomes and the mixture was pre-warmed for 10 minutes. Reactions were initiated by addition of pre-warmed NADPH solution. The final reaction volume was 0.5 mL and contained 50 pmol/mL CYP3A4 Supersomes™, 1.0 mM test compound, and 2 mM NADPH in 0.1 M potassium phosphate buffer, pH 7.4, and 3 mM MgCl$_2$. The reaction mixtures were incubated at 37° C., and 50 mL aliquots were removed at 0, 5, 10, 20, and 30 minutes and added to 96-well plates which contained 50 mL of ice-cold ACN with internal standard to stop the reactions. The plates were stored at 4° C. for 20 minutes after which 100 mL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

Data Analysis:

The in vitro half-lives (t$_{1/2}$ values) for test compounds were calculated from the slopes of the linear regression of LN(% parent remaining) vs incubation time relationship:

in vitro $t_{1/2}$=0.693/k, where k=−[slope of linear regression of % parent remaining (ln) vs incubation time]

FIG. 1 shows a plot of the percentage of parent compound remaining over time for Compound 110 and for ivacaftor in human cytochrome P450-specific SUPERSOMES™. The t$_{1/2}$ values, and the percentage increase (% Δ) in average t$_{1/2}$, are shown in Table 4 below.

TABLE 4

Results of In Vitro Human Cytochrome P450-Specific SUPERSOMES™

| Compound | t$_{1/2}$ (min) | | | AVE ± SD |
| | Experiment 1 | Experiment 2 | Experiment 3 | % Δ |
| --- | --- | --- | --- | --- |
| Ivacaftor | 5.2 | 6.0 | 5.8 | 5.7 ± 0.4 |
| Compound 110 | 9.9 | 7.9 | 8.7 | 8.8 ± 0.8 55% |

Table 4 shows that Compound 110 has a 55% longer half life in the assay than ivacaftor.

Example 6b

Evaluation of Metabolic Stability of Compounds 105 and 106—Human CYP3A4 Supersomes™

Supersomes™ Assay.

7.5 mM stock solutions of test compounds, Compounds 105, 106 and ivacaftor, were prepared in DMSO. The 7.5 mM stock solutions were diluted to 50 mM in acetonitrile (ACN). Human CYP3A4 supersomes (1000 pmol/mL, purchased from BD Gentest™ Products and Services) were diluted to 62.5 pmol/mL in 0.1 M potassium phosphate buffer, pH 7.4, containing 3 mM MgCl$_2$. The diluted supersomes were added to wells of a 96-well polypropylene plate in triplicate. A 10 mL aliquot of the 50 mM test compound was added to the supersomes and the mixture was pre-warmed for 10 minutes. Reactions were initiated by addition of pre-warmed NADPH solution. The final reaction volume was 0.5 mL and contained 50 pmol/mL CYP3A4 Supersomes™, 1.0 mM test compound, and 2 mM NADPH in 0.1 M potassium phosphate buffer, pH 7.4, and 3 mM MgCl$_2$. The reaction mixtures were incubated at 37° C., and 50 mL aliquots were removed at 0, 5, 10, 20, and 30 minutes and added to 96-well plates which contained 50 mL of ice-cold ACN with internal standard to stop the reactions. The plates were stored at 4° C. for 20 minutes after which 100 mL of water was added to the wells of the plate before centrifugation to pellet precipitated proteins. Supernatants were transferred to another 96-well plate and analyzed for amounts of parent remaining by LC-MS/MS using an Applied Bio-systems API 4000 mass spectrometer.

Data Analysis:

The in vitro half-lives (t$_{1/2}$ values) for test compounds were calculated from the slopes of the linear regression of LN(% parent remaining) vs incubation time relationship:

in vitro $t_{1/2}$=0.693/k, where k=−[slope of linear regression of % parent remaining (ln) vs incubation time]

The t$_{1/2}$ values, and the percentage increase (% Δ) in average t$_{1/2}$, for Compounds 105, 106 and for ivacaftor in human cytochrome P450-specific SUPERSOMES™, are shown in Table 5 below.

TABLE 5

Results of In Vitro Human Cytochrome P450-Specific SUPERSOMES™

| Compound | t$_{1/2}$ (min) | | AVE ± SD |
| | Experiment 1 | Experiment 2 | % Δ |
| --- | --- | --- | --- |
| Ivacaftor | 5.5 | 4.9 | 5.2 ± 0.4 |
| Compound 106 | 7.4 | 7.3 | 7.4 ± 0.1 41% |

TABLE 5-continued

Results of In Vitro Human Cytochrome P450-Specific SUPERSOMES ™

| Compound | $t_{1/2}$ (min) | | AVE ± SD |
| --- | --- | --- | --- |
|  | Experiment 1 | Experiment 2 | % Δ |
| Compound 105 | 7.6 | 8.0 | 7.8 ± 0.3 |
|  |  |  | 49% |

Table 5 shows that Compound 106 has a 41% longer half-life in the assay than ivacaftor, and that Compound 105 has a 49% longer half-life than ivacaftor.

Example 7

Evaluation of Pharmacokinetics in Rats for Compounds 105 and 106

Ivacaftor, compound 105 and compound 106 were discrete dosed to rats via oral gavage (PO). Each compound was administered at a dose of 10 mg/kg to three rats (N=3 rats/compound; total of 9 rats in the study). Each compound was formulated in 100% PEG400 at a concentration of 2 mg/mL. Blood samples were collected from each rat at 15 and 30 minutes, and 1, 2, 4, 6, 8, 12, 24, 48, and 72 hours post-dose. Blood samples were centrifuged to obtain plasma. Plasma samples were analyzed for concentrations of the dosed compound at each time point using LC-MS/MS. The limit of quantitation of each compound was 1 ng/mL.

The rat $t_{1/2}$ values (determined by non-compartmental analysis using WinNonlin software) for each compound are shown in Table 6 below:

TABLE 6

| Compd Dosed | Animal ID | $t_{1/2}$ (hr) |
| --- | --- | --- |
| Ivacaftor | 1.1 | 9.03 |
|  | 1.2 | 12.43 |
|  | 1.3 | 10.01 |
|  | Mean | 10.49 |
|  | SD | 1.75 |
|  | SE | 1.01 |
|  | CV % | 16.70 |
| 106 | 2.1 | 13.50 |
|  | 2.2 | 14.28 |
|  | 2.3 | 11.92 |
|  | Mean | 13.24 |
|  |  | (+26%$^a$) |
|  | SD | 1.20 |
|  | SE | 0.69 |
|  | CV % | 9.10 |
| 105 | 3.1 | 13.80 |
|  | 3.2 | 16.33 |
|  | 3.3 | 14.39 |
|  | Mean | 14.84 |
|  |  | (+42%$^a$) |
|  | SD | 1.32 |
|  | SE | 0.76 |
|  | CV % | 8.90 |

$^a$% change relative to ivacaftor $t_{1/2}$ value

Table 6 shows that Compound 106 has a 26% longer mean half-life than ivacaftor, and that Compound 105 has a 42% longer mean half-life than ivacaftor.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

I claim:

1. A compound of Formula I:

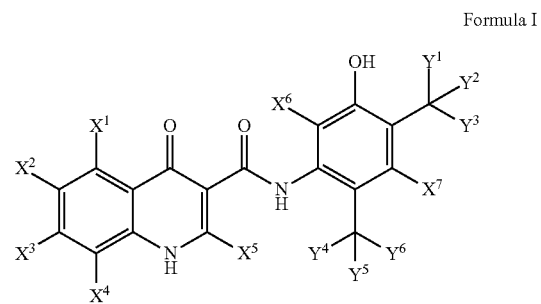

Formula I or a pharmaceutically acceptable salt thereof, wherein
each of $X^1$, $X^2$, $X^3$, $X^4$, $X^5$, $X^6$, and $X^7$ is independently hydrogen or deuterium;
each of $Y^1$, $Y^2$, $Y^3$, $Y^4$, $Y^5$, and $Y^6$ is independently $CH_3$ or $CD_3$;
provided that if each of $Y^1$, $Y^2$, $Y^3$, $Y^4$, $Y^5$, and $Y^6$ is $CH_3$, then at least one of $X^1$, $X^2$, $X^3$, $X^4$, $X^5$, $X^6$, and $X^7$ is deuterium, wherein the isotopic enrichment for each designated deuterium atom is at least 90%.

2. The compound of claim 1, wherein $X^1$, $X^2$, $X^3$, and $X^4$ are each hydrogen.

3. The compound of claim 2, wherein $X^6$ and $X^7$ are each hydrogen.

4. The compound of claim 2, wherein $Y^1$, $Y^2$, and $Y^3$ are the same.

5. The compound of claim 2, wherein $Y^4$, $Y^5$, and $Y^6$ are the same.

6. The compound of claim 1, wherein $X^5$ is deuterium.

7. The compound of claim 3, wherein at least one of $C(Y^1)(Y^2)(Y^3)$ and $C(Y^4)(Y^5)(Y^6)$ is $C(CD_3)_3$.

8. The compound of claim 7, wherein $Y^1$, $Y^2$, and $Y^3$ are $CD_3$.

9. The compound of claim 8, wherein $Y^4$, $Y^5$, and $Y^6$ are $CD_3$.

10. The compound of claim 1, wherein the compound of Formula I is any one of the compounds of the table below,

| Cmpd # | $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
| --- | --- | --- | --- | --- | --- | --- | --- | --- | --- | --- | --- | --- | --- |
| 100 | D | D | D | D | D | D | D | $CD_3$ | $CD_3$ | $CD_3$ | $CD_3$ | $CD_3$ | $CD_3$ |
| 101 | H | H | H | H | D | H | H | $CD_3$ | $CD_3$ | $CD_3$ | $CD_3$ | $CD_3$ | $CD_3$ |
| 102 | H | H | H | H | D | H | H | $CD_3$ | $CD_3$ | $CD_3$ | $CH_3$ | $CH_3$ | $CH_3$ |
| 103 | H | H | H | H | D | H | H | $CH_3$ | $CH_3$ | $CH_3$ | $CD_3$ | $CD_3$ | $CD_3$ |
| 104 | H | H | H | H | D | H | H | $CH_3$ | $CH_3$ | $CH_3$ | $CH_3$ | $CH_3$ | $CH_3$ |

-continued

| Cmpd # | $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|---|
| 105 | H | H | H | H | H | H | H | $CD_3$ | $CD_3$ | $CD_3$ | $CD_3$ | $CD_3$ | $CD_3$ |
| 106 | H | H | H | H | H | H | H | $CD_3$ | $CD_3$ | $CD_3$ | $CH_3$ | $CH_3$ | $CH_3$ |
| 107 | H | H | H | H | H | H | H | $CH_3$ | $CH_3$ | $CH_3$ | $CD_3$ | $CD_3$ | $CD_3$ | or a pharmaceutically acceptable salt thereof, wherein any atom not designated as deuterium is present at its natural isotopic abundance.

11. The compound of claim 1, wherein the compound of Formula I is any one of the compounds of the table below,

| Cmpd # | $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|---|
| 110 | H | H | H | H | H | D | D | $CD_3$ | $CD_3$ | $CD_3$ | $CD_3$ | $CD_3$ | $CD_3$ |
| 111 | H | H | H | H | D | D | D | $CD_3$ | $CD_3$ | $CD_3$ | $CD_3$ | $CD_3$ | $CD_3$ |
| 112 | H | H | H | H | D | D | D | $CD_3$ | $CD_3$ | $CD_3$ | $CH_3$ | $CH_3$ | $CH_3$ |
| 113 | H | H | H | H | D | D | D | $CH_3$ | $CH_3$ | $CH_3$ | $CD_3$ | $CD_3$ | $CD_3$ |
| 114 | H | H | H | H | D | D | D | $CH_3$ | $CH_3$ | $CH_3$ | $CH_3$ | $CH_3$ | $CH_3$ |
| 115 | H | H | H | H | H | D | H | $CD_3$ | $CD_3$ | $CD_3$ | $CH_3$ | $CH_3$ | $CH_3$ |
| 116 | H | H | H | H | H | D | H | $CH_3$ | $CH_3$ | $CH_3$ | $CD_3$ | $CD_3$ | $CD_3$ |
| 117 | D | D | D | D | D | D | D | $CD_3$ | $CD_3$ | $CD_3$ | $CH_3$ | $CH_3$ | $CH_3$ |
| 118 | D | D | D | D | D | D | D | $CH_3$ | $CH_3$ | $CH_3$ | $CD_3$ | $CD_3$ | $CD_3$ |
| 119 | D | D | D | D | D | H | H | $CD_3$ | $CD_3$ | $CD_3$ | $CH_3$ | $CH_3$ | $CH_3$ |
| 120 | D | D | D | D | D | H | H | $CH_3$ | $CH_3$ | $CH_3$ | $CD_3$ | $CD_3$ | $CD_3$ |
| 121 | H | H | H | H | H | H | D | $CD_3$ | $CD_3$ | $CD_3$ | $CD_3$ | $CD_3$ | $CD_3$ |
| 122 | H | H | H | H | H | H | D | $CD_3$ | $CD_3$ | $CD_3$ | $CH_3$ | $CH_3$ | $CH_3$ |
| 123 | H | H | H | H | H | H | D | $CH_3$ | $CH_3$ | $CH_3$ | $CD_3$ | $CD_3$ | $CD_3$ | or a pharmaceutically acceptable salt thereof, wherein any atom not designated as deuterium is present at its natural isotopic abundance.

12. The compound of claim 1, wherein the compound of Formula I is any one of the compounds of the table below,

| Cmpd # | $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|---|
| 124 | H | H | H | H | H | D | H | $CD_3$ | $CD_3$ | $CD_3$ | $CD_3$ | $CD_3$ | $CD_3$ |
| 125 | H | H | H | H | H | D | H | $CD_3$ | $CD_3$ | $CD_3$ | $CH_3$ | $CH_3$ | $CH_3$ |
| 126 | H | H | H | H | H | D | H | $CH_3$ | $CH_3$ | $CH_3$ | $CD_3$ | $CD_3$ | $CD_3$ | or a pharmaceutically acceptable salt thereof, wherein any atom not designated as deuterium is present at its natural isotopic abundance.

13. A pharmaceutical composition comprising a compound of claim 1 or a pharmaceutically acceptable salt thereof; and a pharmaceutically acceptable carrier.

14. A method of treating cystic fibrosis in a subject comprising administering to the subject a compound of Formula I or a pharmaceutical composition comprising a compound of Formula I and a pharmaceutically acceptable carrier, wherein the compound of Formula I has the following structural formula:

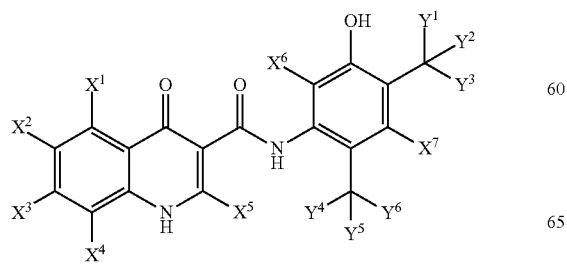

Formula I or a pharmaceutically acceptable salt thereof, wherein each of $X^1$, $X^2$, $X^3$, $X^4$, $X^5$, $X^6$, and $X^7$ is independently hydrogen or deuterium;

each of $Y^1$, $Y^2$, $Y^3$, $Y^4$, $Y^5$, and $Y^6$ is independently $CH_3$ or $CD_3$;

provided that if each of $Y^1$, $Y^2$, $Y^3$, $Y^4$, $Y^5$, and $Y^6$ is $CH_3$, then at least one of $X^1$, $X^2$, $X^3$, $X^4$, $X^5$, $X^6$, and $X^7$ is deuterium, wherein the isotopic enrichment for each deuterium atom in Formula I is at least is 90%.

15. A method of treating COPD in a subject comprising administering to the subject a compound of Formula I or a pharmaceutical composition comprising a compound of Formula I and a pharmaceutically acceptable carrier, wherein the compound of Formula I has the following structural formula:

Formula I

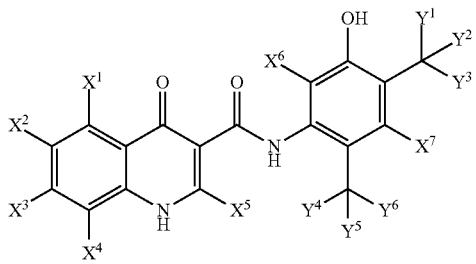

or a pharmaceutically acceptable salt thereof, wherein each of $X^1$, $X^2$, $X^3$, $X^4$, $X^5$, $X^6$, and $X^7$ is independently hydrogen or deuterium;

each of $Y^1$, $Y^2$, $Y^3$, $Y^4$, $Y^5$, and $Y^6$ is independently $CH_3$ or $CD_3$;

provided that if each of $Y^1$, $Y^2$, $Y^3$, $Y^4$, $Y^5$, and $Y^6$ is $CH_3$, then at least one of $X^1$, $X^2$, $X^3$, $X^4$, $X^5$, $X^6$, and $X^7$ is deuterium, wherein the isotopic enrichment for each deuterium atom in Formula I is at least is 90%.

16. The compound of claim 1, wherein the isotopic enrichment for each designated deuterium atom is at least 95%.

17. The method of claim 14, wherein, for the compound of Formula I, the isotopic enrichment for each designated deuterium atom is at least 95%.

18. The method of claim 15, wherein, for the compound of Formula I, the isotopic enrichment for each designated deuterium atom is at least 95%.

\* \* \* \* \*